(12) United States Patent
Hu

(10) Patent No.: US 12,233,420 B2
(45) Date of Patent: Feb. 25, 2025

(54) COLORIMETRIC SENSORS AND METHODS OF MANUFACTURING THE SAME

(71) Applicant: DrinkSavvy, Inc., Brooklyn, NY (US)

(72) Inventor: Min Hu, Brooklyn, NY (US)

(73) Assignee: DrinkSavvy, Inc., Brooklyn, NY (US)

( * ) Notice: Subject to any disclaimer, the term of this patent is extended or adjusted under 35 U.S.C. 154(b) by 70 days.

(21) Appl. No.: 18/336,199

(22) Filed: Jun. 16, 2023

(65) Prior Publication Data

US 2023/0338958 A1    Oct. 26, 2023

Related U.S. Application Data

(63) Continuation of application No. 16/711,843, filed on Dec. 12, 2019, now Pat. No. 11,717,831, which is a continuation of application No. PCT/US2018/037304, filed on Jun. 13, 2018.

(60) Provisional application No. 62/656,860, filed on Apr. 12, 2018, provisional application No. 62/518,903, filed on Jun. 13, 2017.

(51) Int. Cl.
| | |
|---|---|
| *B01L 3/00* | (2006.01) |
| *G01N 21/41* | (2006.01) |
| *G01N 21/65* | (2006.01) |
| *G01N 21/78* | (2006.01) |
| *G01N 33/14* | (2006.01) |

(52) U.S. Cl.
CPC ............ *B01L 3/5085* (2013.01); *G01N 21/41* (2013.01); *G01N 21/65* (2013.01); *G01N 21/78* (2013.01); *G01N 33/14* (2013.01); *B01L 2300/025* (2013.01); *B01L 2300/0663* (2013.01); *B01L 2300/12* (2013.01); *B01L 2300/165* (2013.01)

(58) Field of Classification Search
CPC ............ B01L 3/5085; B01L 2300/025; B01L 2300/0663; B01L 2300/12; B01L 2300/165; G01N 21/41; G01N 21/65; G01N 21/78; G01N 33/14; G01N 21/658; G01N 2021/7723; G01N 21/45; G01N 31/22; G02B 26/005; G02B 1/005; B01J 2220/49; B01J 20/3057; B01J 20/268; B82Y 15/00
See application file for complete search history.

(56) References Cited

PUBLICATIONS

Meng, et al., "Fast screening of ketamine in biological samples based on molecularly imprinted photonic hydrogels", Analytica Chimica Acta, vol. 771, dated Feb. 8, 2013, 9 pages. (Year: 2013).*

* cited by examiner

*Primary Examiner* — Dennis White
(74) *Attorney, Agent, or Firm* — Michael T. Abramson; Jordan IP Law, LLC

(57) ABSTRACT

A colorimetric sensor for detecting an analyte of interest that includes multiple surfaces and a molecularly imprinted polymer defining a cavity shaped to receive an analyte of interest. Each surface defines a void (e.g., a pore or a nanohole) and at least one surface defines a fluid inlet. The sensor is configured such that, when an analyte contacts the molecularly imprinted polymer and becomes disposed within the cavity, a wettability of at least one of the surfaces changes thereby to cause a detectable color change in the sensor. Optionally, the sensor may also include a metal layer at a bottom of each void or nanohole and outside a top of each void or nanohole for use as a plasmon resonance-type sensor.

20 Claims, 17 Drawing Sheets

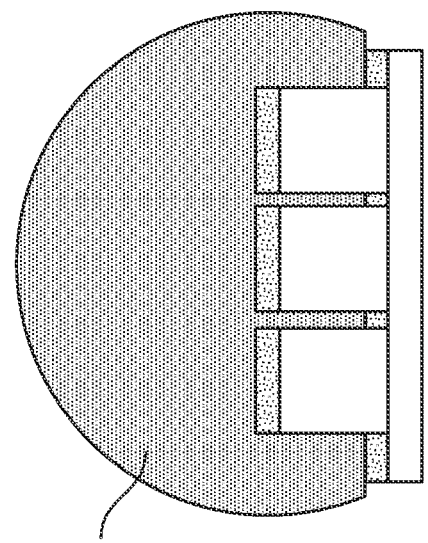
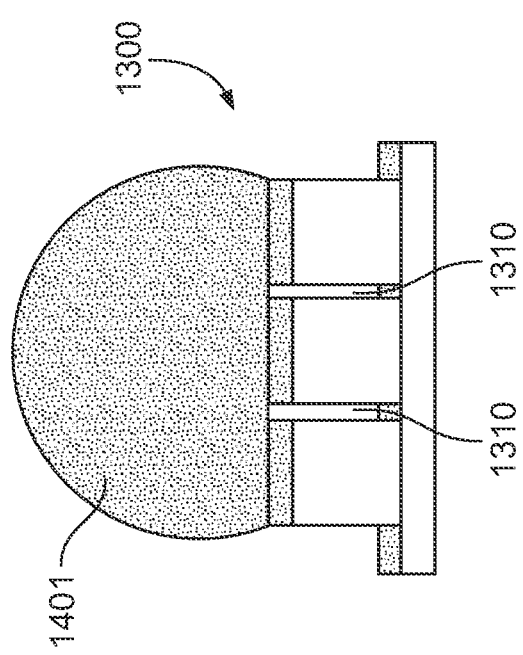

COLORIMETRIC SENSORS AND METHODS OF MANUFACTURING THE SAME

CROSS-REFERENCE TO RELATED APPLICATIONS

This application is a continuation of, claims priority to and the benefit of, and incorporates by reference herein in its entirety U.S. patent application Ser. No. 16/711,843 filed on Dec. 12, 2019, which is a continuation of, claims priority to and the benefit of, and incorporates by reference herein in its entirety International Patent Application No. PCT/US2018/037304, which was filed on Jun. 13, 2018 and which claims priority to and the benefit of U.S. Provisional Patent Application No. 62/518,903, which was filed on Jun. 13, 2017, and U.S. Provisional Patent Application No. 62/656,860, which was filed on Apr. 12, 2018, the contents of which are also incorporated by reference herein in their entireties.

STATEMENT REGARDING FEDERALLY SPONSORED RESEARCH OR DEVELOPMENT

This invention was made with government support under Grant No. 1746719 awarded by the National Science Foundation. The government has certain rights in the invention.

TECHNICAL FIELD

In various embodiments, the present invention relates to a colorimetric sensor for use in detecting the presence of a target molecule (analyte) in a fluid sample and, more specifically, to porous photonic cell colorimetric sensors and plasmonic colorimetric sensors for use in detecting the presence of a target molecule in a fluid sample.

BACKGROUND OF THE INVENTION

The use of agents to incapacitate an individual has become more prevalent. Examples of such agents include gamma-butyrolactone (GBL), gamma-hydroxybutyrate (GHB), ketamine, Rohypnol, and the like. For example, the agents may be secretly placed in a beverage, such as an alcoholic beverage, of the intended consumer. Because these and similar agents are colorless, substantially odorless, and hard to detect, methods and devices are needed to detect the presence of such agents prior to consumption.

Although there are various techniques for detecting the presence of a chemical substance in a subject after the subject has consumed such an agent (e.g., by urinalysis using liquid chromatography-tandem mass spectrometry), such techniques are reactive in nature and merely confirm what may already be suspected, rather than proactive to detect the agent before it has been consumed. Furthermore, such techniques require expensive equipment run by highly trained technicians. Proactive testing devices may require exposing a portion of the liquid to be tested to a chemical reagent composition, which may result in a color change that indicates the presence of the agent in the liquid sample. Unfortunately, such tests are time consuming and may not be discreet.

Additional testing apparatuses are available. For example, a subject may use drug testing strips that are hidden in or incorporated into, for example, a match, a match book, a cocktail napkin, a coaster, a placemat, a menu, and so forth. Although such approaches may appear more discreet, the subject may nevertheless be placed in an awkward position by having to perform the test. Moreover, the subject may have to carry out tests periodically over the course of a social encounter.

U.S. Pat. No. 9,285,352 describes an apparatus for testing a liquid using a straw, a stirrer, and/or a beverage container, where an indicator adapted to provide a visible reaction, e.g., a color change, upon exposure to an agent of interest, is adhered or otherwise bonded to a portion of the straw, stirrer, and/or beverage container. In particular, the indicator may cause the straw, stirrer, and/or beverage container, or the liquid contacting the straw, stirrer, and/or beverage container, to change color and/or fluoresce when an agent of interest is detected at or above a certain concentration.

Despite the advances made to date, there still exists a need for improved devices (e.g., colorimetric sensors) and methods for detecting chemical substances of interest in a liquid sample.

SUMMARY OF THE INVENTION

Embodiments of the invention are based, in part, upon the discovery of a new colorimetric sensor that can detect an analyte of interest in a fluid or liquid sample and that, in some implementations, may be disposed upon or integrated within a surface of a fluid receptacle (e.g., a glass or a cup) or a straw.

In a first aspect, the present invention relates to a colorimetric sensor for detecting an analyte of interest in a fluid sample. In some embodiments, the sensor includes a plurality of surfaces and a molecularly imprinted polymer defining a cavity shaped to receive an analyte of interest. Each surface defines a void and at least one surface defines a fluid inlet. In some implementations, the sensor is configured such that, when an analyte contacts the molecularly imprinted polymer and becomes disposed within the cavity, a wettability of at least one of the plurality of surfaces changes thereby to cause a detectable color change in the sensor. In some applications, the sensor is configured such that, when the cavity receives the analyte, an amount of fluid present in the voids changes, thereby changing a refractive index of at least a portion of the sensor.

In some variations, one or more of the following may apply: a hydrophobic material may be coated on the plurality of surfaces; the sensor may include a solid structure that includes the plurality of surfaces; the molecularly imprinted polymer may be an organic polymer, an inorganic polymer, or a hybrid polymer (including both organic and inorganic components); the molecularly imprinted polymer may be coated on one or more of the plurality of surfaces; the structure may be formed from the molecularly imprinted polymer; the structure may include a dielectric material and/or a metallic material; and/or the structure may include an inverse opal photonic crystal or an inverse opal film. Moreover, in some applications, one or more of the following may apply: each void may be substantially spherically shaped; each void may be substantially cylindrically shaped; at least some of the plurality of voids may be interconnected; the plurality of voids may be isolated from one another; the plurality of voids may have a periodic distribution; neighboring voids may be spaced apart by a distance between 1 nanometer and 1000 nanometers; and/or neighboring voids may be spaced apart by a distance corresponding to a wavelength range of visible light.

In some embodiments, the sensor may also include metal positioned at a bottom of each cylindrically-shaped void and metal positioned outside atop of each cylindrically-shaped void. In some variations, the sensor may be disposed upon or integrated within a surface of a fluid receptacle or a straw.

In a second aspect, the present invention relates to a method for detecting an analyte of interest in a fluid sample. In some embodiments, the method includes the process steps of (a) contacting a colorimetric sensor with the fluid sample and (b) detecting whether a color change occurs when the sensor is contacted with the fluid sample. A color change is indicative that the analyte is present in the fluid sample. In some implementations, the sensor includes a plurality of surfaces and a molecularly imprinted polymer defining a cavity shaped to receive an analyte of interest. Each surface defines a void and at least one surface defines a fluid inlet. In some applications, the sensor is configured such that, when an analyte contacts the molecularly imprinted polymer and becomes disposed within the cavity, a wettability of at least one of the plurality of surfaces changes thereby to cause a detectable color change in the sensor. In some implementations, the sensor is configured such that, when the cavity receives the analyte, an amount of fluid present in the voids changes, thereby changing a refractive index of at least a portion of the sensor.

In some variations, one or more of the following may apply: a hydrophobic material may be coated on the plurality of surfaces; the sensor may include a solid structure that includes the plurality of surfaces; the molecularly imprinted polymer may be an organic polymer, an inorganic polymer, or a hybrid polymer; the molecularly imprinted polymer may be coated on one or more of the plurality of surfaces; the structure may be formed from the molecularly imprinted polymer; the structure may include a dielectric material and/or a metallic material; and/or the structure may include an inverse opal photonic crystal or an inverse opal film. Moreover, in some applications, one or more of the following may apply: each void may be substantially spherically shaped; each void may be substantially cylindrically shaped; at least some of the plurality of voids may be interconnected; the plurality of voids may be isolated from one another; the plurality of voids may have a periodic distribution; neighboring voids may be spaced apart by a distance between 1 nanometer and 1000 nanometers; and/or neighboring voids may be spaced apart by a distance corresponding to a wavelength range of visible light.

In some embodiments, the sensor may also include metal positioned at a bottom of each cylindrically-shaped void and metal positioned outside a top of each cylindrically-shaped void. In some variations, the method further includes confirming that the analyte is present in the fluid sample by using a spectrometer to detect the Raman spectra of the analyte due to the surface enhanced Raman scattering effect.

In a third aspect, the present invention relates to a method of manufacturing a colorimetric sensor capable of detecting an analyte of interest in a fluid sample. In some embodiments, the method includes the process steps of (a) mixing a liquid precursor of a polymer material (e.g., an organic, inorganic, or hybrid polymer material) with a plurality of analytes of interest to create a mixed liquid precursor of the polymer material; (b) co-assembling the mixed liquid precursor of the polymer material with a plurality of templates to create a co-assembly; (c) solidifying the co-assembly; (d) removing the templates from the solidified co-assembly to create a plurality of surfaces for the solidified co-assembly (each of which defines a void in the solidified co-assembly); and (e) removing the analytes from the solidified co-assembly to create a molecularly imprinted polymer defining a plurality of cavities shaped to receive the plurality of analytes, such that, when an analyte contacts the molecularly imprinted polymer and becomes disposed within a cavity, a wettability of at least one of the plurality of surfaces changes thereby to cause a detectable color change in the sensor. In some variations, the method further includes the process step of coating the plurality of surfaces with a hydrophobic material. In some implementations, the co-assembly is solidified via one or more of a thermal treatment, a photo-induced solidification, a radiation-induced solidification, and/or a chemical-reaction-induced solidification.

In some variations, one or more of the following may apply: each template may be substantially spherically shaped or substantially cylindrically shaped; each void may be substantially spherically shaped or substantially cylindrically shaped; at least some of the voids may be interconnected; the voids may be isolated from one another; in solidifying the co-assembly, the templates may be positioned to have a periodic distribution; neighboring templates may be spaced apart by a distance between 1 nanometer and 1000 nanometers; and/or neighboring templates may be spaced apart by a distance corresponding to a wavelength range of visible light.

In some implementations, the method further includes positioning metal at a bottom of each cylindrically-shaped void and outside a top of each cylindrically-shaped void. In some applications, the method further includes disposing the sensor upon or integrating the sensor within a surface of a fluid receptacle (e.g., a cup or a glass) or a straw.

BRIEF DESCRIPTION OF THE DRAWINGS

In the drawings, like reference characters generally refer to the same parts throughout the different views. For the purposes of clarity, not every component may be labeled in every drawing. Also, the drawings are not necessarily to scale, emphasis instead generally being placed upon illustrating the principles of the invention. In the following description, various embodiments of the present invention are described with reference to the following drawings, in which:

FIGS. 14A and 14B schematically illustrate how the colorimetric sensor shown in FIG. 13D operates to detect a fluid containing an analyte of interest, in accordance with some embodiments of the invention.

DETAILED DESCRIPTION

Figure 1A:
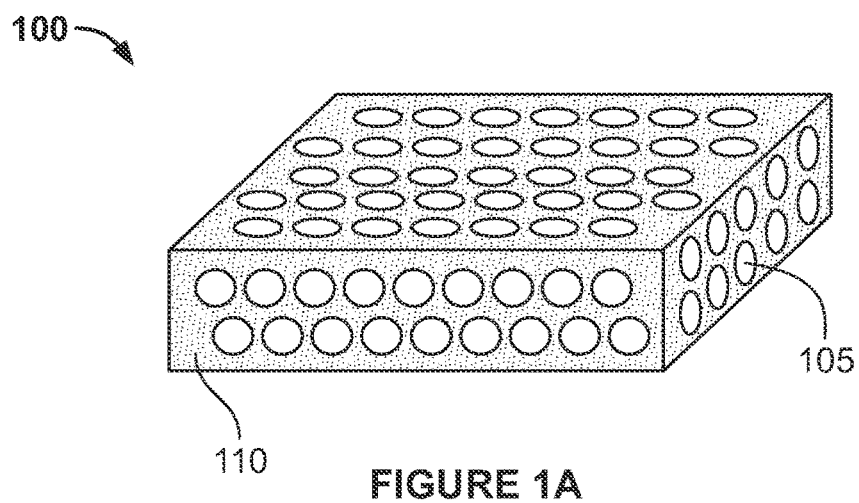
FIG. 1A schematically illustrates a top perspective view of a colorimetric sensor having an array of air voids/pores arranged in a solid structure, in accordance with some embodiments of the invention.

To provide an overall understanding of the invention, certain illustrative embodiments will now be described, including devices (e.g., colorimetric sensors), methods of making the devices, and methods of detecting an analyte target molecule of interest in a fluid sample. However, the devices and methods described herein may be adapted and modified as appropriate for the application being addressed and the devices and methods described herein may be employed in other suitable applications. All such adaptations and modifications are to be considered within the scope of the invention.

Throughout the description, where compositions and devices such as a sensor are described as having, including, or comprising specific components, or where processes and methods are described as having, including, or comprising specific steps, it is contemplated that, additionally, there are compositions and devices of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a device or a method described herein can be combined in a variety of ways without departing from the spirit and scope of the present disclosure, whether explicit or implicit herein. For example, where reference is made to a particular feature, that feature can be used in various embodiments of the devices of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments can be variously combined or separated without parting from the present teachings and disclosure(s). For example, it will be appreciated that all features described and depicted herein can be applicable to all aspects of the disclosure(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also includes the specific quantitative value itself, unless specifically stated otherwise. As used herein, the term "about" refers to a 10% variation from the nominal value unless otherwise indicated or inferred.

Where a percentage is provided with respect to an amount of a component or material in a composition such as a polymer, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remains operable. Moreover, two or more steps or actions can be conducted simultaneously.

At various places in the present specification, features are disclosed in groups or in ranges. It is specifically intended that the description include each and every individual sub-combination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

Various aspects of the disclosure are set forth herein under headings and/or in sections for clarity; however, it is understood that all aspects, embodiments, or features of the disclosure described in one particular section are not to be limited to that particular section but rather can apply to any aspect, embodiment, or feature of the present disclosure.

Structural-Color-Based Colorimetric Sensors

The in-flow and/or presence of a specific fluid, e.g., a fluid containing a target analyte of interest, into the air voids/pores of a three-dimensional ("3D") structure may be used in diagnostic devices, e.g., photonic crystals and other colorimetric sensors, to verify or confirm the presence of the specific fluid. Indeed, and more particularly, a color change detectable in the visible spectrum of light refracted by the structure due to, inter alia, a difference in the refractive index of the structure because of the presence of the fluid in the air voids/pores may be used to identify the nature of the fluid captured in the pores of the structure. Furthermore, by controlling the geometry of the air voids/pores in the 3D structure, as well as the dimensions of any interpore openings, differing structural properties, e.g., surface tension, associated with the specific fluid, at or about the air voids/pores and the interpore openings, may be used to verify or confirm the presence of the target analyte of interest in the sample fluid.

This detectable visible color difference or change in color may be referred to as structural color and may result from coherent visible light wave scattering due to, inter alia, the relationship between structural properties of the specific fluid in the environment of the 3D structure (e.g., the liquid-to-air surface tension, the solid-to-air surface tension, and the solid-to-liquid surface tension) and the periodic surface roughness, porosity, and geometry of the 3D structure, and the like. Others skilled in the art refer to this fluidic light scattering phenomenon as wettability. Wettability may generally be described as a physical property affecting the interaction of a fluid and a solid phase material. For example, wettability provides a measure of the tendency of a specific fluid to spread on, adhere to, be adsorbed by, or the like the surface of a solid structure.

Indeed, recognizing that, when introduced into or proximate air voids/pores in a common 3D structure, different fluids having different structural properties, e.g., surface tension values, may be captured by, adsorbed by, or the like differing wetted surfaces or regions of the air voids/pores within the structure. Colorimetric sensors, using this phenomenon, can, consequently, be designed to detect differences in the wetted surfaces or regions at air voids/pores.

An exemplary, 3D porous photonic cell structure 100 for use as a colorimetric sensor is shown in FIGURE TA. In some applications, the cell structure 100 includes a base substrate 110 that is a solid structure having a plurality of faces. The base substrate 110 of the porous photonic cell 100 may be made of an organic, inorganic, or hybrid molecularly imprinted polymer ("MIP") material (described in greater detail below), of a dielectric or insulative material (e.g., silica, titanium dioxide, silicon nitride, and the like), of a dielectric material coated with a MIP material, of a metallic material (e.g., gold, silver, aluminum, and the like), of a metallic material coated with a MIP material, or any combination thereof.

As illustrated in FIGURE TA, each of the air voids/pores 105 arrayed on the base substrate 110 may generally be described as an open or empty space within the base substrate 110 of the cell structure 100, consisting of or consisting essentially of no other materials than air. In one embodiment, a, e.g., arcuate or spheroidal, surface defines each air void/pore 105. In some embodiments, an array of air voids/pores may be formed in or on one or more of the faces of the base substrate, and, more particularly, on those faces of the base substrate that will be exposed to a sample fluid. Although the air voids/pores 105 shown in certain drawings are spheroidal or substantially spheroidal in shape (see FIGURES TA, 1B, and 3A) and have spheroidal or substantially spheroidal surfaces that define the air voids/pores, those of ordinary skill in the art can appreciate that the air voids/pores may, in the alternative, be cylindrical (see FIG. 4), substantially cylindrical, rectangular, trapezoidal, triangular, polygonal, and so forth.

In some variations of the present invention, each air void/pore may be isolated from other air voids/pores, while, in other variations, selected air voids/pores may be interconnected. The spacing between adjacent air voids/pores may range between about 1 nanometer (nm) and about 1000 nm. Alternatively, the spacing between adjacent air voids/pores may correspond to the wavelength range of visible light. Preferably, there is a periodic distribution among the rows and columns of the air voids/pores.

Figure 2:
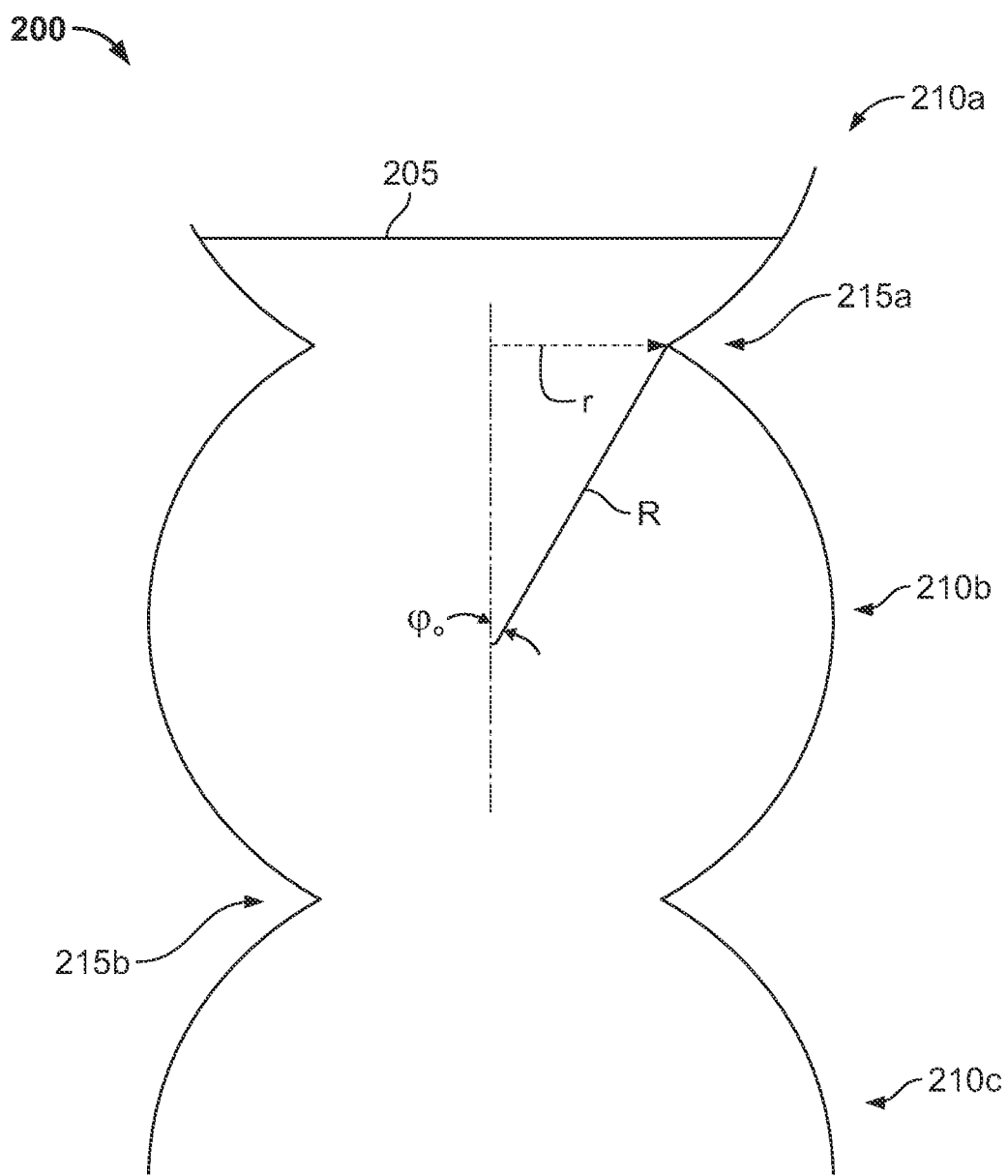
FIG. 2 schematically illustrates a cross-sectional view of a single unit of an inverse-opal film colorimetric sensor, in accordance with some embodiments of the invention.

The cell structure 100 depicted in FIGURE TA may be an inverse opal photonic crystal or an inverse opal film ("IOF"). FIG. 2 provides a schematic cross-sectional view of an exemplary discrete unit cell 210$b$ of, for example, a symmetric IOF 200. In some implementations, the unit cell 210$b$ is disposed between an upper unit cell 210$a$ and a lower unit cell 210$c$. An upper interpore opening 215$a$ separates the unit cell 210$b$ from the upper unit cell 210$a$, while a lower interpore opening 215$b$ separates the unit cell 210$b$ from the lower unit cell 210$c$.

The response of the unit cell 210$b$ in the IOF 200 to the presence of a fluid and fluid pressure at the interpore opening 215$a$ may be determined by the relationship between the critical neck, or intrinsic contact, angle ($\theta_c$) and the neck angle ($\varphi_0$) of the interpore opening 215$a$, which corresponds to the azimuth angle subtended by the interpore opening 215$a$. Whereas the intrinsic contact angle ($\theta_c$) is a function of structural properties (e.g., relative surface tensions) of the fluid and of the IOF 200, the neck angle ($\varphi_0$) of the interpore opening 215$a$ is a function of the structural relationship between the radius of the air void/pore (R) and the radius of the interpore opening (r).

A fluid will not infiltrate into the unit cell 210$b$ as long as the intrinsic contact angle ($\theta_c$) is greater than the neck angle ($\varphi_0$) of the interpore opening 215$a$, or as long as $$\theta_c > \varphi_0. \qquad \text{EQN. 1}$$

On the other hand, a fluid will infiltrate the unit cell 210$b$ as soon as the intrinsic contact angle ($\theta_c$) is less than the neck angle ($\varphi_0$) of the interpore opening 215$a$, or as soon as $$\theta_c < \varphi_0 \qquad \text{EQN. 2}$$

The intrinsic contact angle may be calculated using the formula in EQN. 3 below, while the neck angle may be calculated using the formula in EQN. 4 below.

$$\cos(\theta c) = \frac{(\gamma_{sa} - \gamma_{sl})}{\gamma_{la}} \qquad \text{EQN. 3}$$

in which: $\gamma_{sa}$ refers to the solid-air surface tension of the IOF, $\gamma_{sl}$ refers to the solid-liquid surface tension of the IOF and the fluid, and $\gamma_{la}$ refers to the liquid-air surface tension of the fluid.

$$\sin(\varphi_0) = \frac{r}{R} \qquad \text{EQN. 4}$$

in which: R refers to the radius of the pore of the unit cell 210$b$ and r refers to the neck radius of the interpore opening 215$a$.

EQN. 3 illustrates that the intrinsic contact angle depends on the structural properties of the IOF 200 and of the fluid and, more specifically, on the surface tension relationships of the IOF 200 and the fluid, i.e., the solid-air surface tension, the solid-liquid surface tension, and the liquid-air surface tension. EQN. 4 illustrates that the neck angle depends solely on the dimensions of the unit cell 210$b$ and of the interpore opening 215$a$. Accordingly, as long as the dimensions of the unit cell 210$b$ and the interpore opening 215$a$ can be controlled during manufacture, so as to remain constant, whether or not a fluid infiltrates the unit cell 210$b$ depends on the relative surface tensions of the fluid and the IOF 200 and, more specifically, on changes to the solid-air surface tension, solid-liquid surface tension, and/or liquid-air surface tension. Changes to those surface tensions may result, for example, from the interaction of a specific fluid containing a target analyte(s) of interest with cavities in a MIP material, as described further below. By design, changes to those surface tensions will affect the relationship between the intrinsic contact angle ($\theta_c$) and the neck angle ($\varphi_0$) of the interpore opening 215$a$. In short, the relationship will either allow infiltration (when $\theta_c < \varphi_0$) or prevent infiltration (when $\theta_c > \varphi_0$) and will depend on whether or not the fluid contains a target analyte(s) of interest. Thus, in some embodiments, changes to the solid-air surface tension, solid-liquid surface tension, and/or liquid-air surface tension that result when a target analyte(s) of interest is present in a fluid and, furthermore, captured in or adsorbed by the cavities in an MIP material may effect a decrease in the intrinsic contact angle to allow infiltration (i.e., such that $\theta_c < \varphi_0$).

Hence, although the size and dimensions of the air voids/pores may affect refractive properties, in some embodiments, the structural properties of the specific fluid containing the target analyte(s) of interest and the resulting changes in the structural properties of the MIP material once a cavity or several cavities in the MIP material has/have captured or adsorbed a target analyte(s) of interest ultimately affect whether or not a specific fluid infiltrates the air voids/pores, resulting in structural color changes. In general, the average density of the cavities in the MIP material may be very high (e.g., up to $10^{10}$, $10^{15}$, or $10^{20}$ cavities per gram of MIP material). There may also be some variation in the number, density, and arrangement (e.g., distribution or pattern) of the cavities in the MIP material.

Because infiltration affects whether the specific fluid wets some portion or region of the inner surface defining the air voids/pores and because a discernible color change results from the degree or extent that the air voids/pores are wetted, wettability can be used to identify or confirm the presence (or absence) of a discrete target analyte(s) of interest within a sample fluid. In short, in some implementations, distinct color patterns, i.e., unique colorimetric responses, may be attributable to different fluids due to their ability to infiltrate the air voids/pores when a target analyte(s) of interest is present in the fluid and, furthermore, when the target analyte(s) of interest is captured in and/or adsorbed by the cavities in an MIP material. Hence, those skilled in the art may use such colorimetric sensors to detect, discern, or confirm the presence (or absence) of a target analyte(s) of interest within the fluid sample. Those of ordinary skill in the art can appreciate that, depending on the structural properties of the target analyte of interest in known fluids, as well as the changes in the structural properties of a MIP material once the MIP material captures or adsorbs the target analyte(s) in one or more cavities, the IOF may be designed such that the presence of the target analyte of interest causes the fluid to infiltrate the unit cell $215b$ ($\theta_c < \varphi_0$).

With reference again to FIG. 2, in operation, a first fluid 205 in a first IOF 200 will not infiltrate or descend into the unit cell $210b$ until EQN. 2 is true (or, equivalently, until EQN. 1 is not true). Therefore, as long as EQN. 2 is not true (or, equivalently, EQN. 1 is true), a first wetted region associated with the IOF 200 will be confined, for example, to the upper unit cell $210a$ and to the interpore opening $215a$ region. This may be referred to as an unfilled state. The wettability, and therefore the light refracted by the IOF 200, will differ when EQN. 2 becomes true (or, equivalently, when EQN. 1 becomes not true) and the fluid 205 in the IOF 200 infiltrates or descends into the unit cell $210b$. When the fluid 205 infiltrates the unit cell $210b$, this may be referred to as the filled state or, in some instances, the substantially, or partially, filled state. A partially filled state may exist when the fluid 205 is able to infiltrate the unit cell $210b$, but there is insufficient fluid 205 to completely fill the unit cell $210b$. In either of the filled or partially filled states, the fluid infiltration wets a larger region or portion of the IOF 200, e.g., the upper unit cell $210a$, the unit cell $210b$, and the interpore opening $215a$ region, than was the case associated with the unfilled state. As a result of this wettability, the light refracted by the IOF 200 will differ from the previous (unfilled) instance. The phenomenon of wettability, therefore, enables designers to design a colorimetric sensor 100 that uses structural color associated with wettability to discern, verify, or confirm the presence of a target analyte(s) of interest in a fluid sample.

In some implementations, and with reference again to FIGURE TA, in order to ensure that all fluids which do not contain a target analyte of interest are prevented from infiltrating the air voids/pores 105, the surficial walls defining each of the air voids/pores 105 may be coated with a hydrophobic material (e.g., Teflon, silane, or the like). This hydrophobic material repels, in the first instance, all fluids which do not contain a target analyte of interest and thereby prevents them from infiltrating the air voids/pores 105.

Figure 1B:
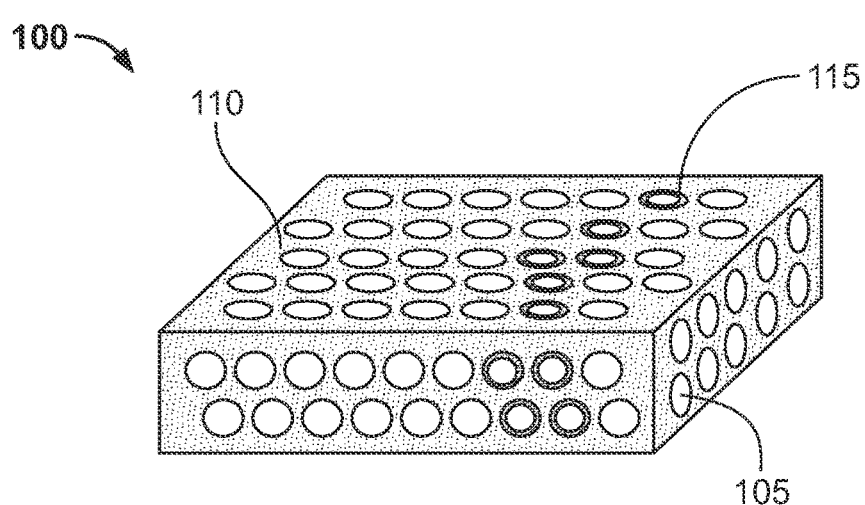
FIG. 1B schematically illustrates a top perspective view of the colorimetric sensor of FIGURE TA in which a molecularly imprinted polymer (MIP) material has been formed (e.g., coated) on some portion of the surface of selected air voids/pores, in accordance with some embodiments of the invention.

With reference to FIG. 1B, however, the surficial walls defining all or a select number of the air voids/pores 105 in the base substrate 110 may additionally be coated with one or more thin layers of organic, inorganic, or hybrid molecularly imprinted polymer (MIP) materials 115. Alternatively, the coatings 115 may include or be aptamer materials or other binding materials such as coordination complex. The thickness of the coatings 115 may range from, e.g., 1 Angstrom (e.g., in the case of a molecular monolayer) up to a thickness approaching a radius of the air voids/pores 105.

Figure 1C:
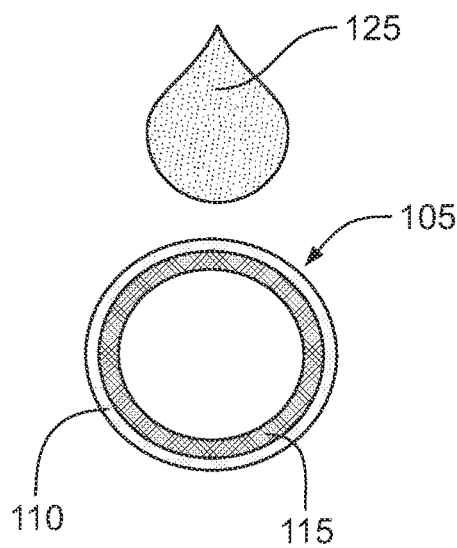
FIG. 1C schematically illustrates a cross-sectional view of an unfilled fluid state within one of the MIP-coated air voids/pores formed in the sensor of FIG. 1B in the presence of a fluid that does not contain a target analyte of interest, in accordance with some embodiments of the invention.
Figure 1D:
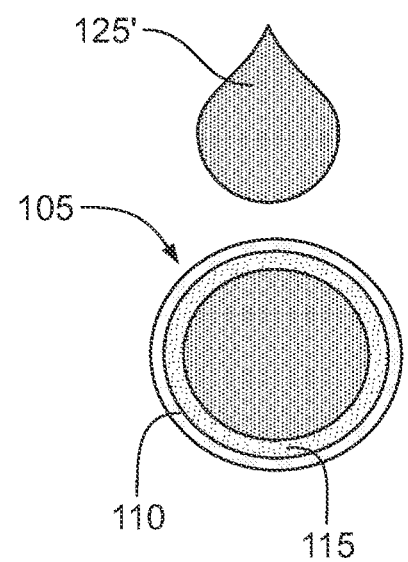
FIG. 1D schematically illustrates a cross-sectional view of a filled fluid state within one of the MIP-coated air voids/pores formed in the sensor of FIG. 1B in the presence of a fluid that contains a target analyte of interest and adsorption of the fluid to wet some portion of the MIP-coated surface, in accordance with some embodiments of the invention.
Figure 1E:
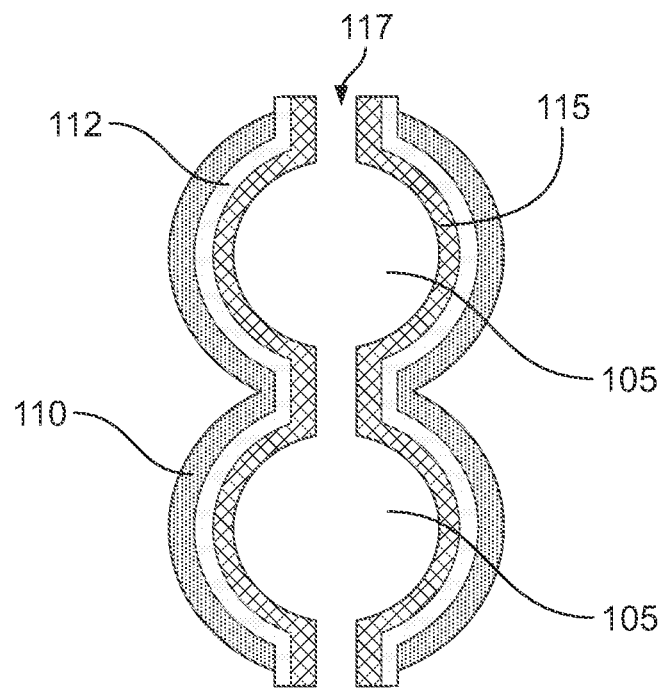
FIG. 1E schematically illustrates a cross-sectional view of two air voids/pores that are each coated with both a hydrophobic material and a MIP material, in accordance with some embodiments of the invention.
Figure 1F:
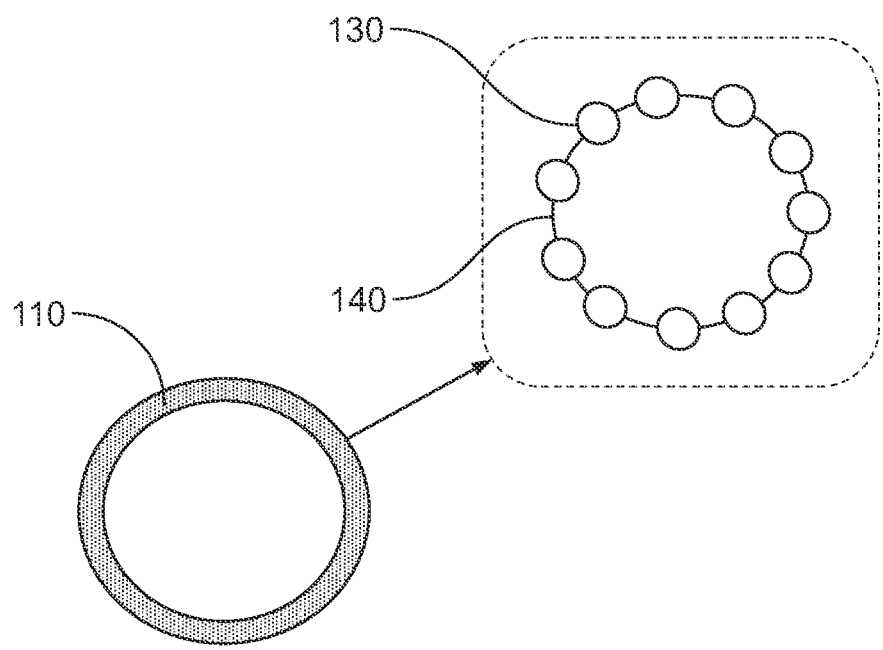
FIG. 1F schematically illustrates a cross-sectional view of an air void/pore and includes a detail of the surficial wall defining the air void/pore being doped with metal nanoparticles, in accordance with some embodiments of the invention.

FIG. 1E depicts exemplary air voids/pores 105 of a base substrate 110 in which the surficial walls defining the air voids/pores 105 are coated with a hydrophobic material 112 and MIP materials 115. As described below, upon absorbing a target analyte(s) of interest, the MIP coatings 115 modify the wettability of the surfaces upon which they are coated to a degree great enough to overcome the initial hydrophobicity of the surfaces and thereby allow infiltration of a fluid containing the target analyte(s) of interest into (e.g., via a fluid inlet 117) the air voids/pores 105 that are coated with the MIP materials 115. In a non-limiting example, as illustrated in FIG. 1F, the base substrate 110 may be doped with metal nanoparticles or partially coated with metal so that parts of the surficial walls defining the air voids/pores 105 are metallic surfaces 130 exposed to air and other parts of the surficial walls are non-metallic (e.g., silica, titanium dioxide, hafnium oxide, etc.) surfaces 140 exposed to air prior to the surfaces 130, 140 being coated/functionalized with the hydrophobic layer 112 and MIP materials 115. In some embodiments, during the subsequent coating process, the MIP materials 115 are coated on the metallic surfaces 130, while the hydrophobic layer 112 is coated on the non-metallic surfaces 140.

In greater detail, with reference to FIG. 1C, a first fluid 125 that does not contain a target analyte(s) of interest is prevented from infiltrating into any of the air voids/pores 105 coated with the hydrophobic material, including those air voids/pores that are also coated with the MIP layer 115. In particular, because the first fluid 125 does not contain an analyte of interest, the cavities in the MIP material 115 do not absorb any analytes of interest, and the solid-air surface tension, solid-liquid surface tension, and liquid-air surface tension do not change to the extent needed (if at all) to modify the wettability of the surfaces defining the air voids/pores 105 upon which the MIP material is coated so that infiltration of the first fluid 125 is enabled (i.e., $\theta_c > \varphi_0$). For the exemplary sensor depicted in FIGS. 1B and 1C, then, non-infiltration indicates that the target analyte(s) of interest is not present in the first fluid 125.

In contrast, as shown in FIG. 1D, when a second fluid $125'$ containing a target analyte(s) of interest is introduced into or brought into the proximity of the same porous photonic cell 100, the target analyte(s) of interest may be captured in or adsorbed by one or more cavities in the solid MIP coating material 115. Advantageously, the capture/adsorption of the target analyte(s) of interest in one or more of the cavities of the MIP material 115 coated on the surficial walls of the air voids/pores 105 changes the nature of the solid MIP material. These changes also change the structural properties, e.g., the solid-air surface tension and the solid-liquid surface tension, of the solid, MIP material 115. As a result, the change in surface tension values associated with the solid material (i.e., the MIP material), coupled with the change in the liquid-air surface tension value due to the second fluid $125'$ containing the target analyte(s) of interest, will, in correctly-designed applications, cause the intrinsic contact angle ($\theta_c$) to be less than the neck angle ($\varphi_0$), so that the second fluid $125'$ infiltrates the air voids/pores 105. Thus, as a result of this capture or adsorption of the target analyte(s) of interest in the second fluid $125'$ by the MIP layers 115, all or some portion or region of the MIP-coated surficial wall of the air void/pore 105 will, in comparison with the previous example, be wetted or have a wetted perimeter. Advantageously, this wettability modification induces a change of filling status from an unfilled state (FIG. 1C) to a fully filled or substantially fully filled state (FIG. 1D), resulting in an observable structural color change displayed by the photonic cell 100 (e.g., the introduction of the fluid $125'$ into the air voids/pores 105 changes a local refractive index of those air voids/pores 105, resulting in the structural color change).

Figure 3A:
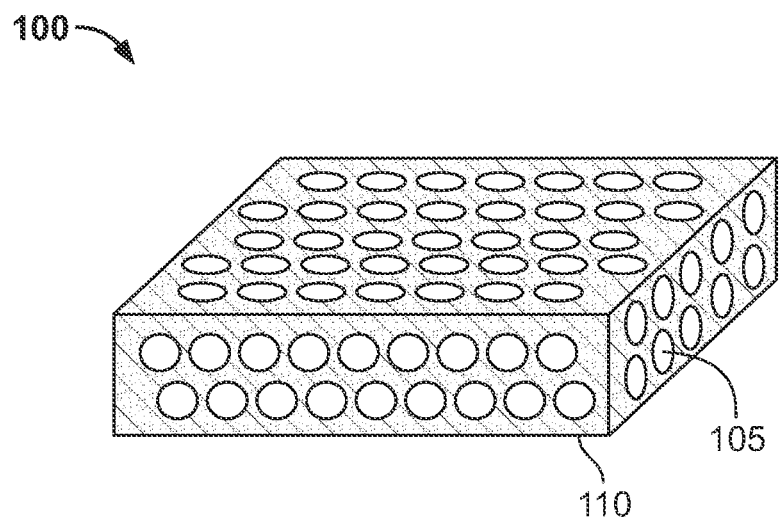
FIG. 3A schematically illustrates a top perspective view of the colorimetric sensor of FIGURE TA in which the solid structure is formed from a MIP material and the air voids/pores are formed into the MIP material, in accordance with some embodiments of the invention.
Figure 3B:
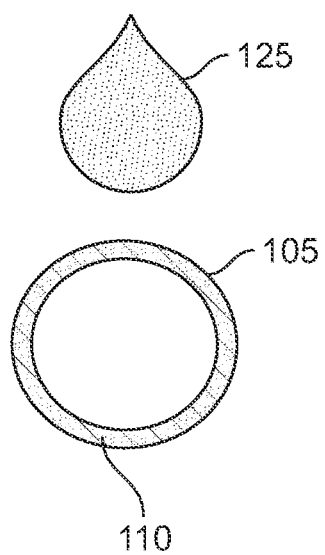
FIG. 3B schematically illustrates a cross-sectional view of an unfilled fluid state within one of the air voids/pores formed in the sensor of FIG. 3A in the presence of a fluid that does not contain a target analyte of interest, in accordance with some embodiments of the invention.

In a second embodiment, as shown in FIG. 3A, instead of coating the surficial walls of the air voids/pores 105 formed in the base substrate 110 with one or more MIP layers, the solid structure of the base substrate 110 of the colorimetric sensor 100 is made entirely or substantially from a MIP material. Moreover, as before, the surficial walls defining each of the air voids/pores 105 may be coated with a hydrophobic material (e.g., Teflon, silane, or the like). Accordingly, as was the case in FIG. 1B, a first fluid 125 that does not contain a target analyte(s) of interest (FIG. 3B) is repelled by the hydrophobic material and is prevented from infiltrating into any of the air voids/pores 105, which therefore remain in an unfilled state.

Figure 3C:
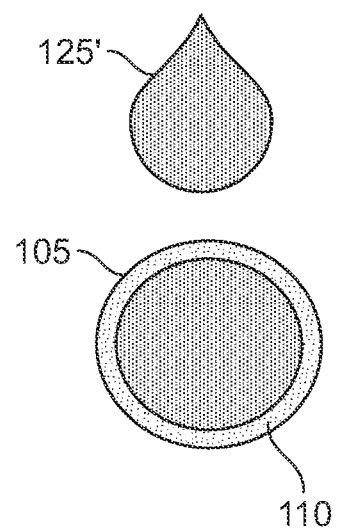
FIG. 3C schematically illustrates a cross-sectional view of a filled fluid state within one of the air voids/pores formed in the sensor of FIG. 3A in the presence of a fluid that contains a target analyte of interest and adsorption of the fluid to wet some portion of the MIP surface, in accordance with some embodiments of the invention.

In contrast, as shown in FIG. 3C, when a second fluid 125' containing a target analyte(s) of interest is introduced into or brought into the proximity of the same porous photonic cell 100, the target analyte(s) of interest may be captured in or adsorbed by one or more of the cavities in the MIP material (e.g., the chosen hydrophobic materials are porous enough and thin enough to allow the target analyte(s) of interest to pass therethrough to the MIP material). Advantageously, the capture/adsorption of the target analyte(s) of interest in one or more of the cavities of the MIP material changes the nature of the MIP material at the surficial walls of the air voids/pores 105. This change also changes the structural properties, e.g., the solid-air surface tension and the solid-liquid surface tension, of the MIP material. As a result, the change in surface tension values associated with the solid material (i.e., the MIP material), coupled with the change in the liquid-air surface tension value due to the second fluid 125' containing the target analyte(s) of interest, will, in correctly-designed applications, cause the intrinsic contact angle ($\theta_c$) to be less than the neck angle ($\varphi_0$), so that the second fluid 125' infiltrates the air voids/pores 105. Thus, as a result of this capture or adsorption of the target analyte(s) of interest in the second fluid 125' by the MIP material, all or some portion or region of the surficial walls of the air voids/pores 105 will, in comparison with the previous example, be wetted or have a wetted perimeter. Advantageously, this wettability modification induces a change of filling status from an unfilled state (FIG. 3B) to a fully filled or substantially fully filled state (FIG. 3C), resulting in an observable structural color change displayed by the photonic cell 100 (e.g., the introduction of the fluid 125' into the air voids/pores 105 changes a local refractive index of those air voids/pores 105, resulting in the structural color change).

Figure 4:
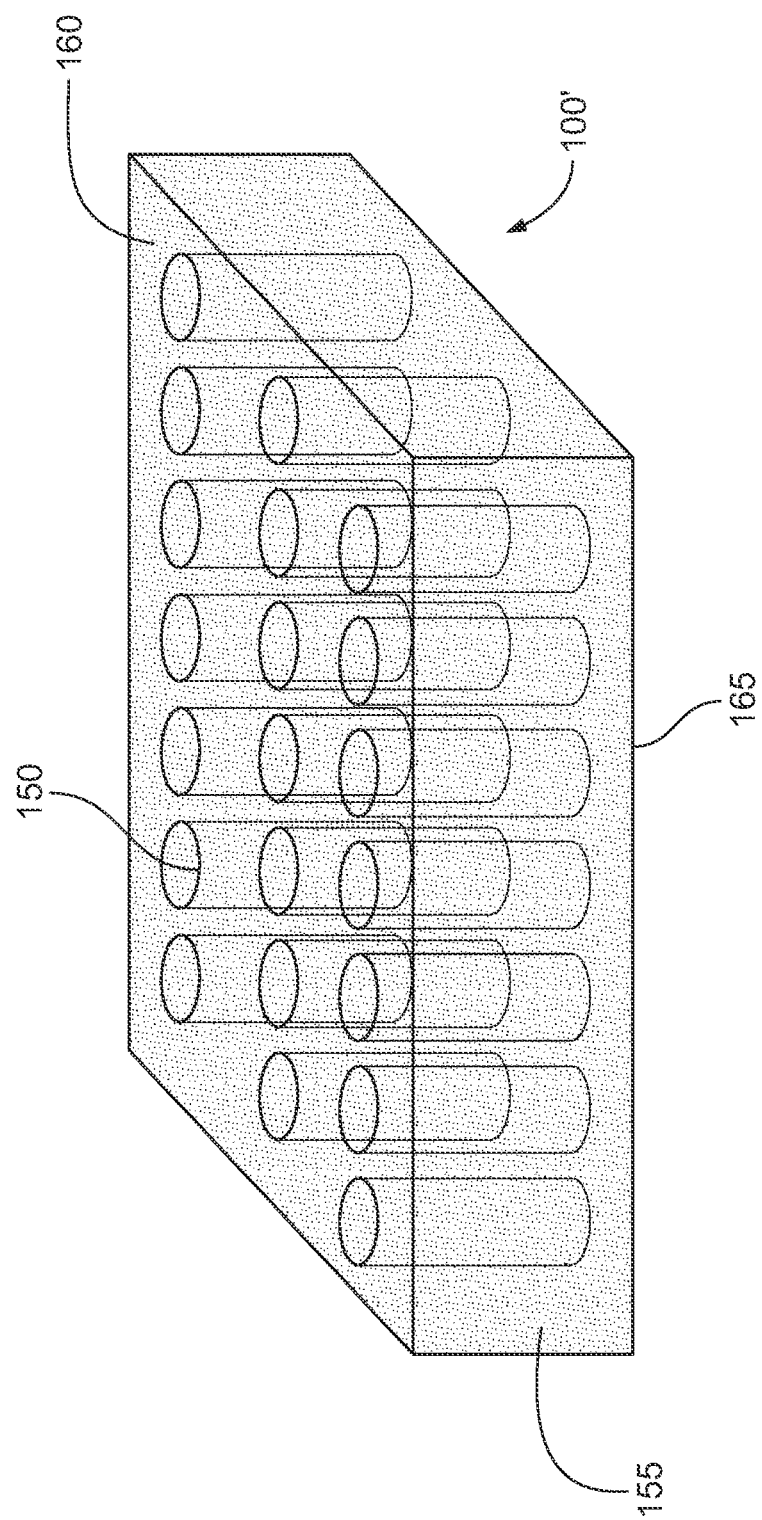
FIG. 4 schematically illustrates a top perspective view of a colorimetric sensor having an array of cylindrically shaped or substantially cylindrically shaped voids (e.g., nanoholes) arranged in a solid structure, in accordance with some embodiments of the invention.

Referring to FIG. 4, in yet another embodiment, a colorimetric sensor 100' may include a plurality of surfaces defining an array of cylindrical or substantially cylindrical air voids (e.g., nanoholes) 150 in a base substrate 155. The base substrate 155 of the colorimetric sensor 100' may be made of an organic, inorganic or hybrid MIP material, of a dielectric or insulative or semiconductor material (e.g., silica, titanium dioxide, silicon nitride, silicon, and the like), of a dielectric material coated with a MIP material, of a metallic material (e.g., gold, silver, aluminum, and the like), of a metallic material coated with a MIP material, or any combination thereof.

Although the cylindrical or substantially cylindrical nanoholes 150 in FIG. 4 appear to extend from one face, e.g., the top face 160, of the base substrate 155 to a second face, e.g., the bottom face 165, this is done for illustrative purposes only. In alternative embodiments, a first array of cylindrical or substantially cylindrical nanoholes 150 may be formed in the top face 160 and a second array of cylindrical or substantially cylindrical nanoholes 150 may be formed in the bottom face 165 of the base substrate 155, such that some portion of the base substrate 155 separates the bottoms of each of the cylindrical or substantially cylindrical nanoholes 150 formed in the top face 160 from the bottoms of each of the cylindrical or substantially cylindrical nanoholes 150 formed in the bottom face 165. In yet another variation, cylindrical or substantially cylindrical nanoholes 150 may be formed on other faces of the base substrate 155, in lieu of or including the top 160 and bottom faces 165.

Although the equations above were derived for application in connection with spheroidal air voids/pores, those of ordinary skill in the art can appreciate that the phenomenon of wettability may also be used in connection with non-spheroidal air voids, including cylindrical or substantially cylindrical nanoholes. Indeed, fluids having different surface tension properties will infiltrate or not infiltrate a common opening to produce a greater or lesser wetted surface or region within the cylindrical or substantially cylindrical nanoholes. As before, a change in the amount of the surface wetted in the nanohole(s) (due to the infiltration of a fluid) produces a detectable structural color change.

In some implementations, the surficial walls defining each of the cylindrical or substantially cylindrical nanoholes in the base substrate may be coated with a hydrophobic material and the surficial walls defining all or a selected number of the cylindrical or substantially cylindrical nanoholes in the base substrate may also be coated with one or more thin layers of MIP materials (or aptamer materials or other binding materials such as coordination complex), as was the case in FIG. 1B. Alternatively, instead of coating the surficial walls of the cylindrical or substantially cylindrical nanoholes formed in the base substrate with one or more MIP materials (or aptamer materials or other binding materials such as coordination complex), the base substrate may be made entirely or substantially from a MIP material and the surficial walls defining each of the cylindrical or substantially cylindrical nanoholes may be coated with a hydrophobic material, as was the case in FIG. 3A. In either case, the colorimetric sensor 100' depicted in FIG. 4 functions as earlier described. In particular, if a fluid does not contain an analyte of interest, the MIP cavities do not absorb any analytes of interest, and the solid-air surface tension, solid-liquid surface tension, and liquid-air surface tension values do not change to the extent needed (if at all) to modify the wettability of the surfaces defining the cylindrical or substantially cylindrical nanoholes so that infiltration of the fluid into the nanoholes is enabled. On the other hand, if a fluid does contain the analytes of interest, the MIP cavities absorb the analytes of interest, and the solid-air surface tension, solid-liquid surface tension, and liquid-air surface tension values change to the extent needed to enable infiltration of the fluid into the nanoholes. The resulting change from an unfilled to partially or fully filled state then results in an observable structural color change displayed by the colorimetric sensor 100' (e.g., the introduction of the fluid into the nanoholes changes a local refractive index of those nanoholes, resulting in the structural color change).

Methods of Manufacturing the Structural-Color-Based Colorimetric Sensors

The porous photonic cell-type colorimetric sensors described herein may be manufactured in a variety of manners. The colorimetric sensor depicted in FIG. 1B, for example, may be manufactured by applying a hydrophobic coating or layer and a MIP coating or layer to an existing inverse opal photonic crystal or inverse opal film, which are structures that are well known in the art.

The hydrophobic coating may be applied to the surficial walls defining each of the air voids/pores in a variety of manners. For example, where the hydrophobic coating includes silane molecules, the hydrophobic coating may be applied via vapor phase deposition. As additional examples, where the hydrophobic coating includes dielectric materials (e.g., titanium dioxide, silicon dioxide, hafnium oxide, etc.), the hydrophobic coating may be applied via atomic layer deposition (ALD), plasma-enhanced chemical vapor deposition (PECVD), or physical vapor deposition (PVD). As yet another example, where the hydrophobic coating includes metallic materials (e.g., gold, silver, aluminum, copper, etc.), the hydrophobic coating may be applied via an electron-beam evaporation process.

Several approaches exist for manufacturing a MIP layer. In some embodiments, the MIP material for a MIP coating or a MIP layer may be manufactured by polymerization, e.g., by thermal and/or photochemical initiation, of a mixture of monomers, cross-linkers, initiators, and/or porogens, or combinations thereof and the like. The choice of components for the mixture depends on the type and end use of the MIP material. Typical monomers include, for the purpose of illustration and not limitation, carboxylic acids (e.g., acrylic acid, methacrylic acid, vinylbenzoic acid, and trifluoromethyl acrylic acid (TFMAA)), sulphonic acids (e.g., 2-acrylamido-2-methylpropane sulphonic acid), heteroaromatic bases (e.g., vinylpyridine and vinylimidazole), acrylamide, 2-hydroxyethylmethacrylate (HEMA), and the like. Typical cross-linkers include, for the purpose of illustration and not limitation, ethylene glycol dimethacrylate (EGDMA), trimethylolpropane trimethacrylate (TRIM), divinylbenzene (DVB), pentaerythritol triacrylate (PETRA), and the like. Typical initiators include, for the purpose of illustration and not limitation, acetyl peroxide, lauroyl peroxide, decanoyl peroxide, caprylyl peroxide, benzoyl peroxide, tertiary butyl peroxypivalate, sodium percarbonate, tertiary butyl peroctoate, azobis-isobutyronitrile (AIBN), and the like. Typical porogens include, for the purpose of illustration and not limitation, methanol, acetonitrile, toluene, mineral oil, and combinations thereof.

Figure 5:
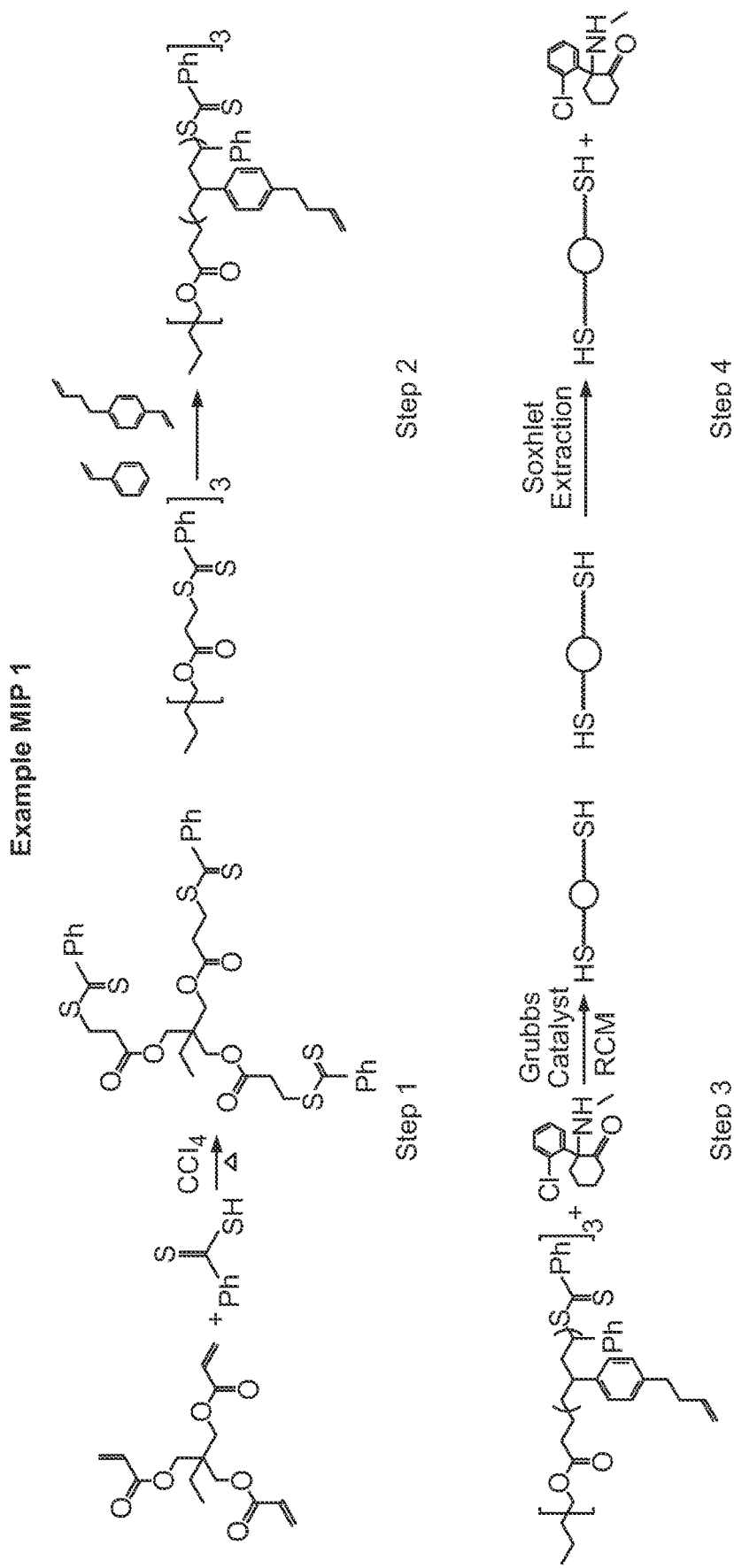
FIG. 5 schematically illustrates a first method of manufacturing a MIP layer for application as a coating on some portion of the surface of selected air voids/pores in the colorimetric sensor of FIG. 1B, in accordance with some embodiments of the invention.

In some embodiments, a MIP layer or coating may be applied as a coating to the surficial walls defining all or a select number of the air voids/pores. In various embodiments, a soluble and processable MIP layer is developed as shown in FIG. 5. In general, the soluble and processable MIP layer is made from a polymer with cross-linkable arms, e.g., a star-shaped polymer with cross-linkable arms, or a dendrimer with cross-linkable arms. The cross-linkable arms may contain one or more vinyl groups or other suitable functional groups that may be initiated and/or participate in a polymerization reaction. In FIG. 5, ketamine is used as an example target analyte for the molecularly imprinting process to produce the MIP, but other target analytes may also be used. In greater detail, the soluble and processable MIP layer may be made from crosslinkable star polymers synthesized using controlled free radical polymerization methods such as RAFT (reversible-addition fragmentation chain-transfer) or ATRP (atom transfer radical polymerization), or by grafting end-functionalized polymer chains onto a multifunctional central core. The polymerization may incorporate a functional monomer into the chain that can be used to form crosslinks (e.g., 4-butenylstyrene, 2-(allyloxy)ethyl acrylate, and N-(hex-5-enyl)acrylamide). Crosslinking the star polymer in the presence of the target analytes of interest may form selective receptor binding sites around the target analytes. Crosslinking may be accomplished catalytically (e.g., cross-metathesis of olefin-terminated side chains). The terminal functional groups may allow the MIP polymers or coating or layer to be bound to the porous photonic cell-type colorimetric sensor surface. As non-limiting examples, thiol groups facilitate bonding to metal surfaces, and polymers functionalized with a silanizing reagent may bond to glass. The MIP layer may be attached to the photonic cell surfaces using, for example, covalent bonds, non-covalent forces, ionic bonds, van der Waals forces, electrostatic forces, hydrogen bonding, Pi-Pi stacking interactions, and the like.

In certain embodiments, the soluble and processible MIP coating layer can be replaced by a coating of aptamers or other binding materials such as coordination complex that specifically bind to analyte molecules. Aptamers are oligonucleotide molecules that bind to a specific target molecule and they can be produced in a process similar to a molecularly imprinted polymer. For example, ketamine can be used as the analyte template to form aptamers via an imprinting and SELEX (systematic evolution of ligands by exponential enrichment) process to determine the desired oligonucleotide sequence. The terminal functional groups may be modified to allow the coating of aptamers to be bound to the porous photonic cell-type colorimetric sensor surface.

Figure 6:
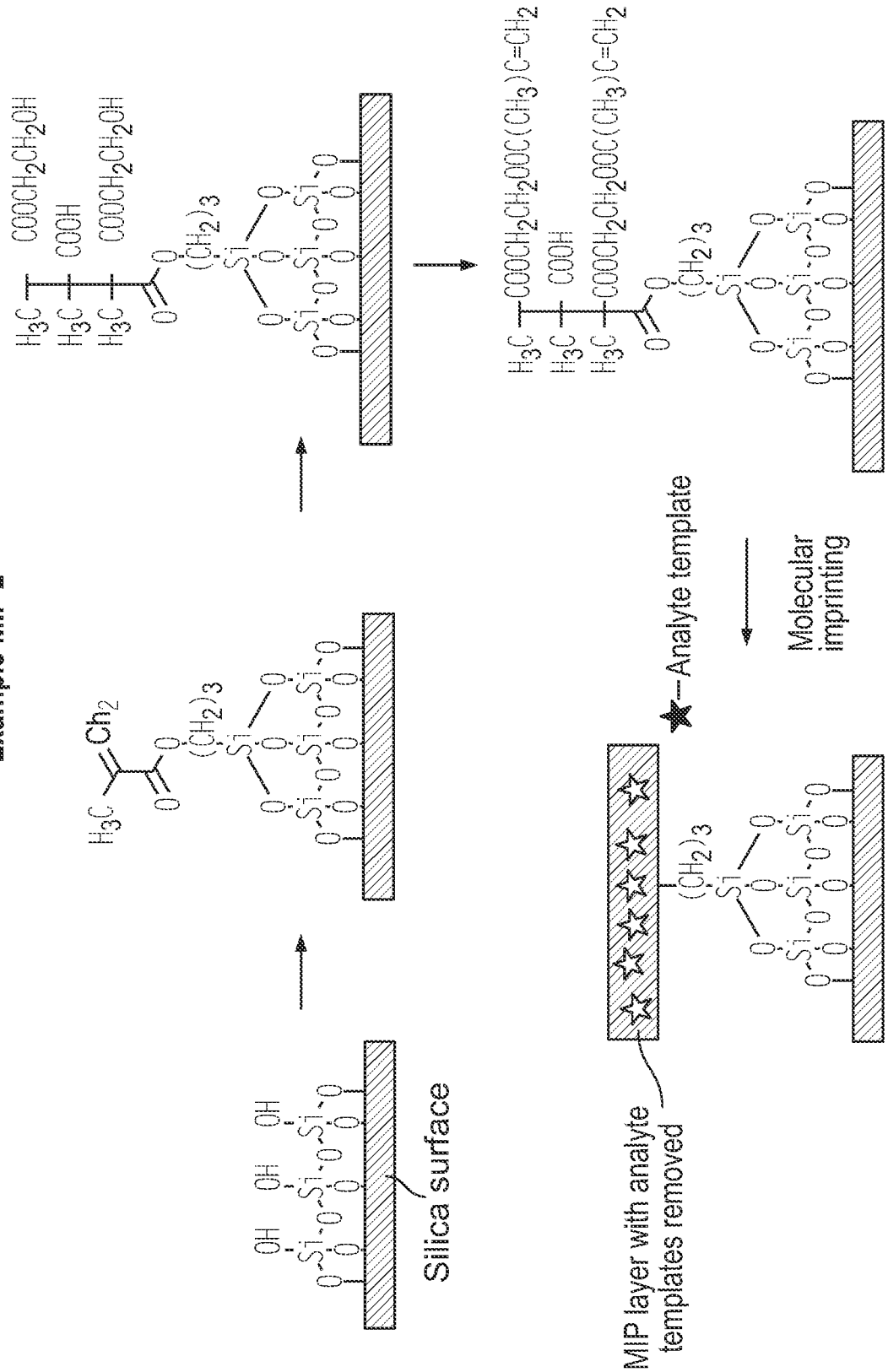
FIG. 6 schematically illustrates a second method of manufacturing a MIP layer for application as a coating on some portion of the surface of selected air voids/pores in the colorimetric sensor of FIG. 1B, in accordance with some embodiments of the invention.

In some embodiments, the MIP layer may be produced, grown, or grafted in situ on the inner surfaces or surficial walls of the photonic cell. An exemplary grafting process is illustrated in FIG. 6. As a non-limiting example, a silanization process is employed to functionalize the silica surface, e.g., of an inverse opal photonic crystal or film, with vinyl groups, from which a macromonomer can be grown via a "grafted" approach (as shown in the top row of FIG. 6 to the structure in the bottom row, right hand side). Target analyte molecules can be subsequently imprinted in situ in a MIP thin layer, e.g., using the soluble and processible MIP approach described herein, where the MIP thin layer may be on and/or attached to the surface of the silica of the inverse opal photonic crystal or film. Subsequently, the target analyte molecules may be removed to form the MIP thin layer (as shown in the structure in the bottom row, left hand side of FIG. 6).

For its part, the colorimetric sensor 100 depicted in FIG. 3A (including base substrate 110 and air voids/pores 105) may be, for example, synthesized from a homogenous liquid precursor of a polymer material, which may be an organic, inorganic, or hybrid polymer material, under suitable reaction conditions. As a non-limiting example, where the base substrate is or includes silica, the base substrate may be formed from its sol-gel precursor tetraethyl orthosilicate (TEOS) under suitable conditions. As another non-limiting example, where the base substrate is or includes titanium dioxide, the base substrate may be formed from its precursors tetraiso-propylorthotitanate (i.e., $Ti(OC_3H_7)_4$ or "TIPT") and/or titanium tetrachloride (i.e., $TiCl_4$) under suitable conditions.

In greater detail, in accordance with a method of manufacturing the colorimetric sensor of FIG. 3A, a liquid precursor of the appropriate organic, inorganic, or hybrid (e.g., TEOS, (3-aminopropyl)triethoxysilane (APTES), or suitable silane molecules) polymer material may be mixed homogeneously with target analyte molecules of interest that act as templates for molecularly imprinting purposes, e.g., to create cavities for recognition of the target analyte molecule. In some embodiments, this mixed liquid precursor of the organic, inorganic or hybrid polymer material may be mixed with and include porogens (e.g., nanospheres, microspheres, etc.), which may be fugitive materials, for creating the air voids/pores. The shape of the air voids/pores may be spherical or whatever is the shape of the porogen. The mixed liquid precursor also can include metal nanoparticles (e.g., gold, silver, and/or platinum nanoparticles) via a sol-gel process.

The mixed liquid precursor then may be solidified under suitable reaction conditions, such as under moderate temperature (e.g., a temperature from room temperature to 300° C.), to lock in the porogens in periodic positions (e.g., such that neighboring porogens are spaced apart by a distance between 1 nanometer and 1000 nanometers or by a distance corresponding to a wavelength range of visible light). Solidification methods may include, but are not limited to, thermal treatment, photo-induced solidification, radiation-induced solidification, and chemical reaction-induced solidification. In some embodiments, the target analyte molecules of interest that act as cavity templates are then removed to form the molecularly imprinted cavities of the MIP. Analyte molecule templates may be removed using, for example, a Soxhlet extraction process, a sonication process, a washing process with suitable solvent (e.g., methanol/acetic acid or other solvents and combinations thereof). The porogens that form the spherical or other shaped air voids/pores, such as colloidal porogens (e.g., spherical latex nanoparticles) may be removed using a thermal process (e.g., sintering above 500° C.) or by dissolution using a suitable solvent or solvent system. As previously described, at least some of the resulting spherical or other shaped air voids/pores may be interconnected or, alternatively, the resulting spherical or other shaped air voids/pores may be isolated from one another. Moreover, as described, the porogens used to form the air voids/pores may have a shape other than spherical (e.g., cylindrical or another shape) such that the resulting air voids/pores have a shape other than spherical (e.g., cylindrical, as depicted in FIG. 4, or another shape similar to the shape of the porogen used).

After the base substrate 110 is synthesized as described herein, for example, which base substrate could be a MIP, a hydrophobic coating may be applied to the surficial walls defining each of the air voids/pores in a variety of manners. For example, where the hydrophobic coating includes silane molecules, the hydrophobic coating may be applied via vapor phase deposition. As additional examples, where the hydrophobic coating includes dielectric materials (e.g., titanium dioxide, silicon dioxide, hafnium oxide, etc.), the hydrophobic coating may be applied via atomic layer deposition (ALD), plasma-enhanced chemical vapor deposition (PECVD), or physical vapor deposition (PVD). As yet another example, where the hydrophobic coating includes metallic materials (e.g., gold, silver, aluminum, copper, etc.), the hydrophobic coating may be applied via an electron-beam evaporation process.

Plasmonic-Resonance-Based Colorimetric Sensors

Surface plasmon resonance ("SPR") is a phenomenon that generally occurs when incident light strikes a metallic surface, where electromagnetic fields, e.g., an electromagnetic surface wave, are very strong. Advantageously, spectral properties of the resonance, e.g., a plasmonic scattering profile resulting from reflected light waves having discrete wavelengths, may be used to characterize the local environment, especially after the metallic nanoparticle surface and, more particularly, electrons located on the surface of the nanoparticle, i.e., the surface plasmons, have been excited by the incident light. For example, incident light, striking near or between metallic nanoparticle surfaces and having a specific wavelength, excites surface plasmons, causing them collectively to oscillate. This oscillation generates a significantly enhanced electromagnetic field. The added presence of analyte target molecules that adhere to or are associated with the metallic nanoparticle surfaces modify the local dielectric environment, further inducing a plasmonic scattering profile change that, advantageously, may lead to enhanced macroscopic color change that can be used to detect and/or confirm the presence of an analyte target molecule in a fluid sample.

In the structure and design of plasmonic colorimetric sensors, the scattered, reflected, or transmitted color is determined, e.g., primarily or at least in part, by a localized plasmon resonance between two metal surfaces separated by a coupling distance. According to the Mie theory, the size and shape of the metal surfaces affect plasmon resonance. Periodicity between adjacent metal surfaces also affects plasmon resonance. For example, the closer the metallic surfaces are to each other, the greater the coupling between the interacting dipoles of the two metallic surfaces. The greater the interactive dipole coupling, the greater the increase of the plasmon resonant wavelength. In contrast, the more distant the metallic surfaces are from one another, the weaker the coupling between the interacting dipoles, resulting in a decrease of the plasmon resonant wavelength.

Figure 7:
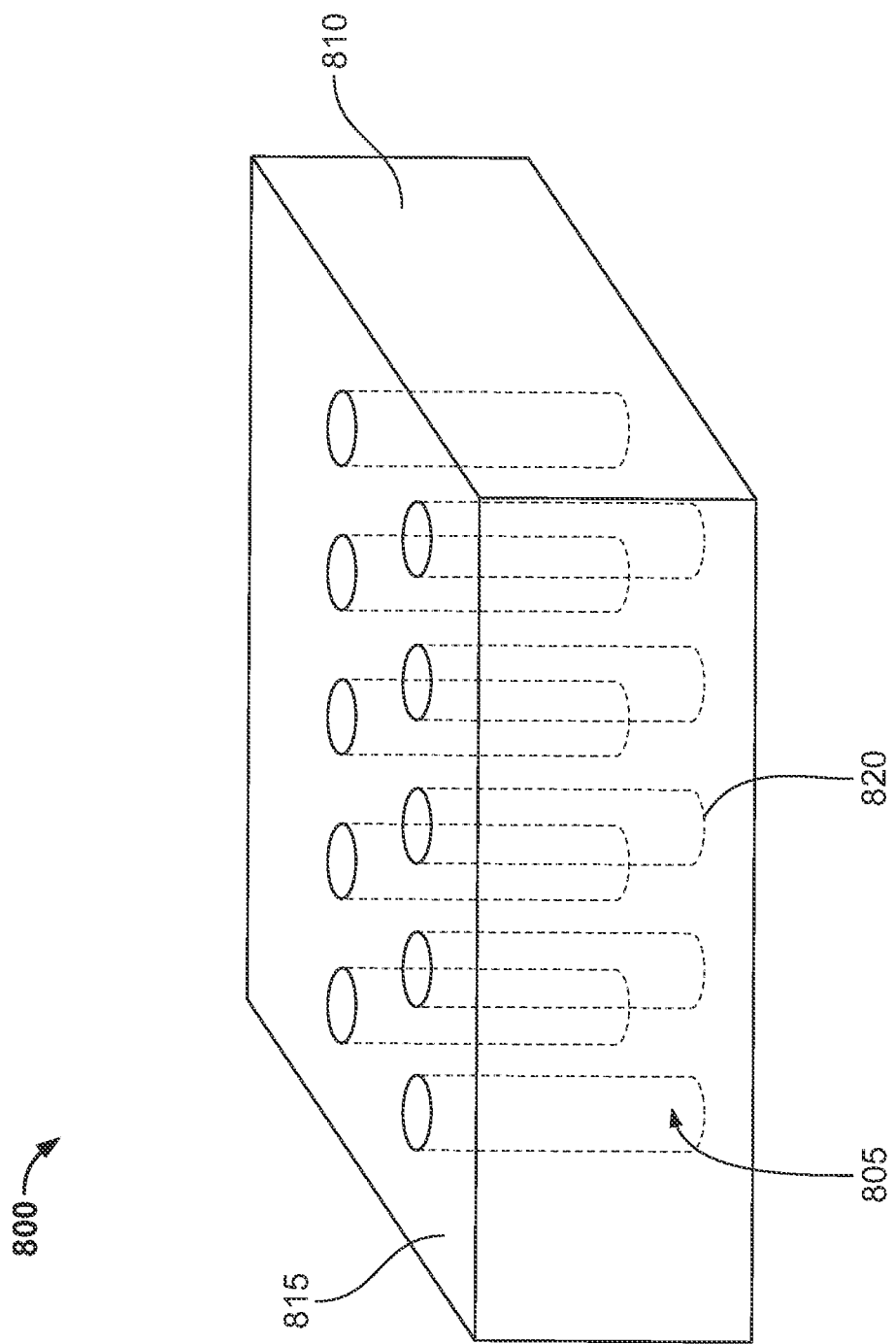
FIG. 7 schematically illustrates a top perspective view of a plasmon resonance-type colorimetric sensor having a plurality of voids (e.g., nanoholes) arrayed in a base substrate, in accordance with some embodiments of the invention.
Figure 8A:
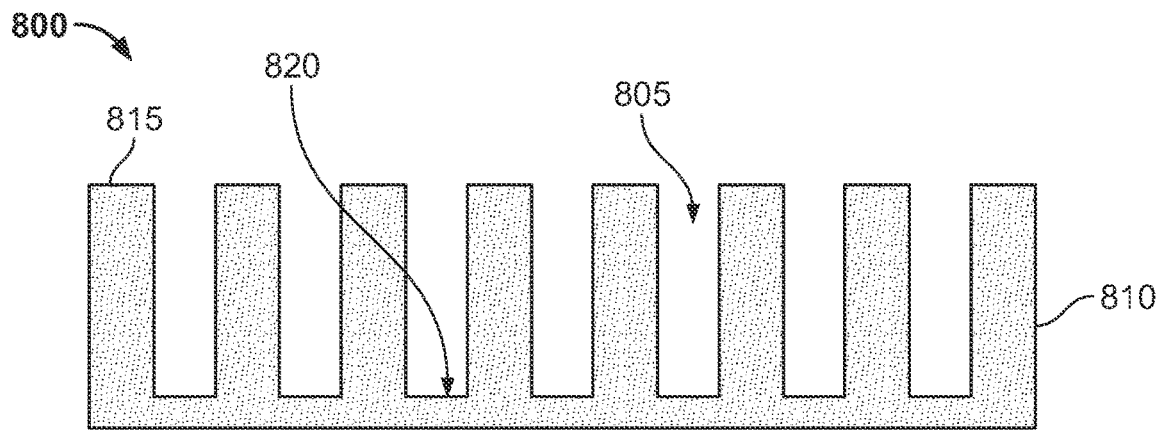
FIG. 8A schematically illustrates a cross-sectional view of a plasmon resonance-type sensor having a plurality of voids (e.g., nanoholes) arrayed in a base substrate, in accordance with some embodiments of the invention.
Figure 8B:
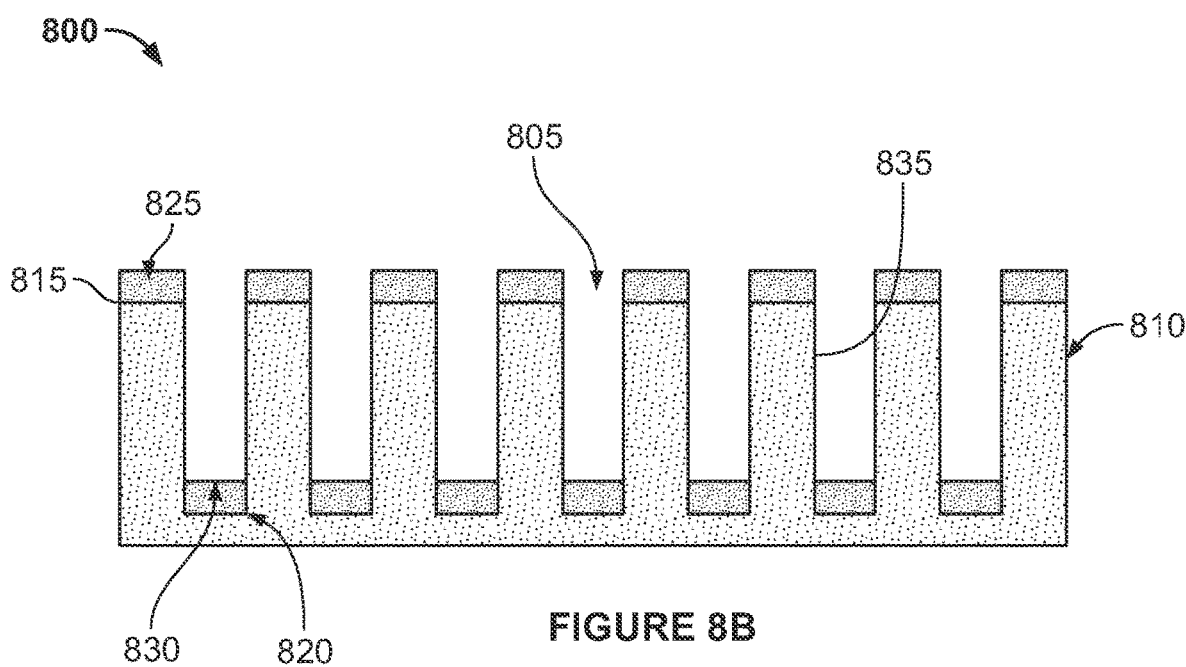
FIG. 8B schematically illustrates a cross-sectional view of a plasmonic resonance-type colorimetric sensor having a plurality of voids (e.g., nanoholes) arrayed in a base substrate with metallic deposits about the nanoholes at the surface of the base substrate and at the bottom of the nanoholes, in accordance with some embodiments of the invention.

In some embodiments, the plasmonic colorimetric sensors described herein define a periodic array of air voids (e.g., nanoholes) in a base substrate. For such sensors, the nanoholes may be used to provide the coupling distance between two metallic surfaces. A first embodiment of a plasmon resonance colorimetric sensor 800 having an array of cylindrical or substantially cylindrical nanoholes 805 is depicted in FIGS. 7, 8A, and 8B.

In some embodiments, the array of nanoholes 805 is formed in a base substrate 810. The depth of the nanoholes 805 may be used to provide the coupling distance between two metallic surfaces 825, 830 that may be formed on, for example, an upper surface 815 of the base substrate 810 and a bottom 820 of each nanohole 805. The metallic surfaces 825, 830 may be made from, for example, platinum, gold, silver, aluminum, copper, tungsten, and combinations thereof, and may be relatively thin (e.g., each surface 825, 830 may be 0.1 nm to several hundreds of nanometers thick). For ease of illustration, the metallic surfaces 825, 830 are only shown in FIG. 8B, although in practice the metallic surfaces 825, 830 would be present in each of the devices depicted in FIGS. 7, 8A, and 8B. The arrayed nanoholes 805 and metallic surfaces 825, 830 of the embodied sensor 800 provide a plurality of metal-insulator-metal (MIM) antenna structures 835 in the base substrate 810.

The metallic surfaces provide vertical limits for collecting and focusing incident light. With only the metallic surface 825 present, for example, the optical scattering intensity would be very low, making it difficult to observe the scattered color. By combining the metallic surface 825 with the metallic surfaces 830, however, plasmonic coupling between the upper and lower components typically increases or enhances the scattering intensity and the hues. Advantageously, plasmonic coupling between the metallic surfaces may result in a vibrant color without viewing angle dependence.

For the purpose of illustration and not limitation, the nanoholes in the plasmonic colorimetric sensors may be formed in the base substrate in, for example, a patterned grid, such that each nanohole has the same or substantially the same size, e.g., dimensions (height and width), and shape (e.g., cylindrical or substantially cylindrical), and such that the spacing between adjacent nanoholes is periodic. Those of ordinary skill in the art can appreciate that the number and arrangement of the nanoholes, as well as the size, shape, and the like of each nanohole and the periodicity between adjacent nanoholes may be subject to the design and purpose of the plasmonic colorimetric sensor.

Although FIG. 7 depicts cylindrically-shaped or substantially-cylindrically-shaped nanoholes 805, that is done for the purpose of illustration and not limitation. Indeed, in addition to being cylindrical, the nanoholes may be rectangular or of other shapes. Typical depths for nanoholes may range between about one (1) nm and about one (1) mm, or between about 5 nm and about 1000 nm, or between about 10 nm and about 500 nm. Typical diameters for cylindrical nanoholes may range between about 10 nm and about 5000 nm, or between about 15 nm and about 750 nm, or between about 20 nm and about 500 nm. Typical spacing between adjacent nanoholes may range between about 1 nm and about 5000 nm, or between about 1 nm and about 1000 nm, or between about 20 nm and about 500 nm. In some implementations, adjacent or neighboring nanoholes may be spaced a distance corresponding to a wavelength range of visible or infrared light.

In various embodiments, the base substrate may be manufactured from an organic, inorganic, or hybrid MIP material, from a dielectric or insulative material (e.g., silica, titanium dioxide, silicon nitride, and the like) in which the plurality of surfaces defining the nanoholes are coated with a MIP or aptamer material or other binding material such as coordination complex, or from a metallic material (e.g., gold, silver, aluminum, and the like) in which the plurality of surfaces defining the nanoholes are coated with a MIP or aptamer material or other binding material such as coordination complex. Preferably, the MIP material defines cavities for attracting and capturing and/or for adsorbing discrete analyte target molecules. In general, the average density of the cavities in a MIP material may be very high (e.g., up to $10^{10}$, $10^{15}$, or $10^{20}$ cavities per gram of MIP material).

The plasmonic colorimetric sensors may be configured to produce, in the presence of an analyte target molecule(s) and when struck by incident light of a particular wavelength, an observable change in color within the visible spectrum. Indeed, as described herein, when incident light of a particular wavelength strikes the MIM antenna structures, the light scattered by the plasmonic colorimetric sensors will produce an observable color change, providing evidence of the presence of the analyte target molecule(s).

In some applications, the MIP material, layer, and/or coating may generally be manufactured by polymerization, e.g., by thermal and/or photochemical initiation, of a mixture of monomers, cross-linkers, initiators, and/or porogens, or combinations thereof and the like. Typical monomers include, for the purpose of illustration and not limitation, carboxylic acids (e.g., acrylic acid, methacrylic acid, vinylbenzoic acid, and trifluoromethyl acrylic acid (TFMAA)), sulphonic acids (e.g., 2-acrylamido-2-methylpropane sulphonic acid), heteroaromatic bases (e.g., vinylpyridine and vinylimidazole), acrylamide, 2-hydroxyethylmethacrylate (HEMA), and the like. Typical cross-linkers include, for the purpose of illustration and not limitation, ethylene glycol dimethacrylate (EGDMA), trimethylolpropane trimethacrylate (TRIM), divinylbenzene (DVB), pentaerythritol triacrylate (PETRA), and the like. Typical initiators include, for the purpose of illustration and not limitation, acetyl peroxide, lauroyl peroxide, decanoyl peroxide, caprylyl peroxide, benzoyl peroxide, tertiary butyl peroxypivalate, sodium percarbonate, tertiary butyl peroctoate, azobis-isobutyronitrile (AIBN), and the like. Typical porogens include, for the purpose of illustration and not limitation, methanol, acetonitrile, toluene, mineral oil, and combinations thereof.

In some implementations, the base substrate (e.g., if made entirely from a MIP) or a coating therefor (e.g., if the surfaces of the base substrate defining the nanoholes are coated with a MIP) defines cavities produced by, for example, removing template molecules from the MIP materials. In some variations, the cavities are shaped to receive discrete analyte target molecules. The cavities can be formed in a MIP by removing the analyte templates from the MIP. The MIPs formed in this way may include a soluble and processible MIP synthesized (as a non-limiting example) following the four steps depicted in FIG. 5. Note that this is just an example as MIPs can be created using other forms of polymerization. The MIP materials may be attached to metallic surface areas via graft-to or graft-from methods.

Referring again to FIGS. 7, 8A, and 8B, the surficial walls defining each of the nanoholes 805 in the base substrate 810 may be coated with a hydrophobic material (e.g., after the metallic surfaces 825, 830 have been deposited). In such a fashion, if a fluid does not contain an analyte of interest, the MIP cavities do not absorb any analytes of interest, the fluid is repelled by the hydrophobic material, and the fluid is prevented from infiltrating into any of the nanoholes 805, which therefore remain in an unfilled state. On the other hand, if a fluid does contain the analytes of interest, the MIP cavities absorb the analytes of interest, and the solid-air surface tension, solid-liquid surface tension, and liquid-air surface tension values change (i.e., the wettability of the surficial walls defining the nanoholes 805 changes) to the extent needed to enable infiltration of the fluid into the nanoholes 805.

Accordingly, when an analyte target molecule is adsorbed into or bound to a MIP cavity, several changes occur to produce an observable color change in the plasmonic-resonance-based colorimetric sensor 800 of FIGS. 7, 8A, and 8B. First, the effective refractive index in the localized environment changes due to the infiltration of the fluid into the nanoholes 805 and due to the presence of the analyte target molecule in the MIP material. In many cases, this change in the effective refractive index affects the dipole interaction between the metallic surfaces 825, 830. This dipole interaction determines the scattered hybridized plasmon resonance, i.e., the color. Second, adsorption of the analyte to the cavities may cause the MIP materials of the base substrate 810 or coating therefor to swell (e.g., increase in height), which, in turn, may modify, i.e., increase, the coupling distance between the metallic surfaces 825, 830. Increasing the coupling distance between the two metallic surfaces decreases the coupling between the interacting dipoles of the metallic surfaces, thereby decreasing the plasmon resonant wavelength. In turn, the reduced plasmon resonant wavelength leads to an observable color change in the colorimetric sensor.

The binding of analyte target molecules can thus result in an observable color change, e.g., from blue to red, within the visible light spectrum. Advantageously, the initial color before analyte binding may be tuned and optimized by varying the size and shape of the nanoholes, as well as by varying the periodicity of the nanoholes on the sensor.

Although the illustrative embodiment of a plasmon resonance colorimetric sensor has been depicted and described for instances in which the nanoholes formed in a single base substrate share the same or substantially the same size, shape, periodicity, and so forth, those of ordinary skill in the art can appreciate that, in some applications of the present invention, one or more groupings of nanoholes may be formed on the base substrate, such that one or more of the properties or parameters of one of the nanohole groupings intentionally differs from the properties or parameters of another of the nanohole groupings, so as to produce different changes in the colors emitted by the various nanohole groupings on the same substrate. Indeed, at a microscopic (e.g., pixel and sub-pixel) level, a first nanohole grouping, having a first set of design and structural properties, may be formed or disposed on a first portion of the base substrate so as to emit, under a first set of operating conditions, a first color, while, under the same first set of operating conditions, a second nanohole grouping, having a second set of design and structural properties and formed or disposed on a second portion of the base substrate, emits a second color that differs from the first color. Under a second set of operating conditions, the individual microscopic colors emitted by the first and second nanostructure groupings may produce a color change that, at the macroscopic level of the array, becomes more pronounced or more distinct.

Figure 9A:
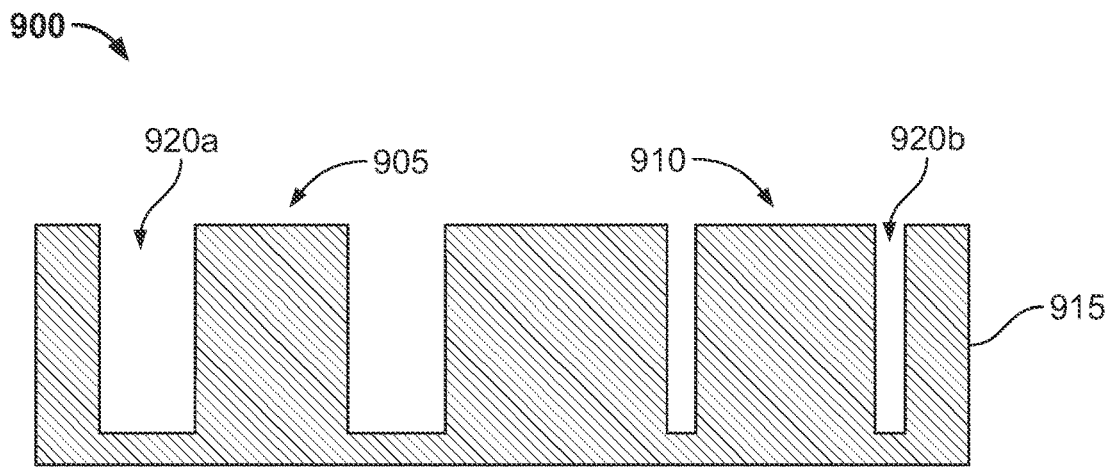
FIG. 9A schematically illustrates a cross-sectional view of a dual or side-by-side surface plasmon resonance-type colorimetric sensor having a first sub-pixel array of a plurality of voids (e.g., nanoholes) arrayed in a first region of the base substrate and a second sub-pixel array of a plurality of voids (e.g., nanoholes) arrayed in a second region of the base substrate, in accordance with some embodiments of the invention.
Figure 9B:
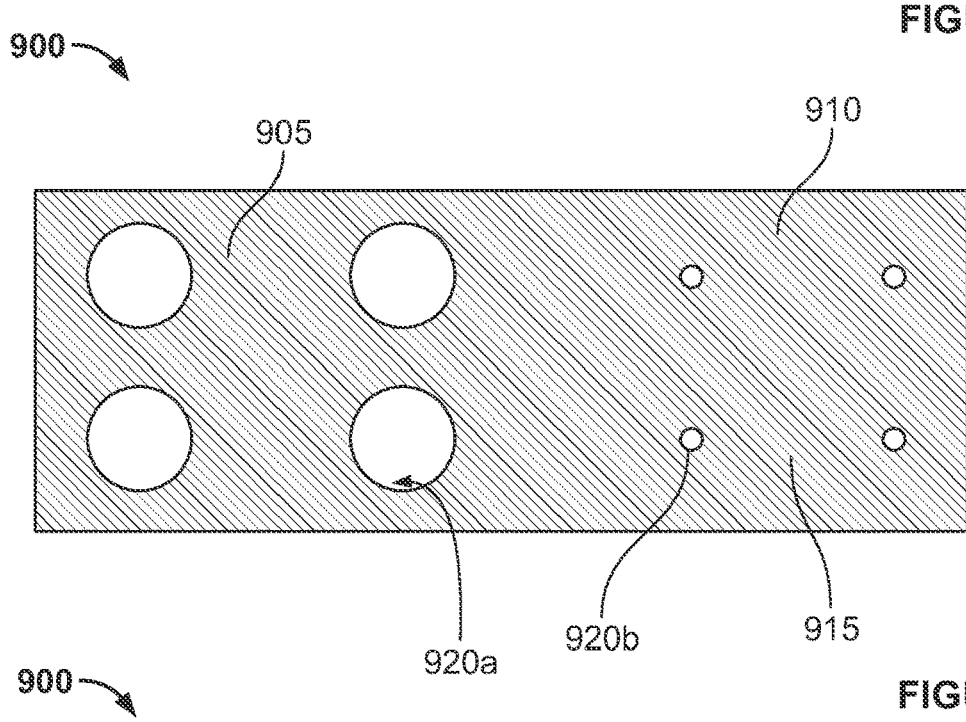
FIG. 9B schematically illustrates a plan view of the dual or side-by-side surface plasmon resonance-type colorimetric sensor of FIG. 9A, in accordance with some embodiments of the invention.
Figure 9C:
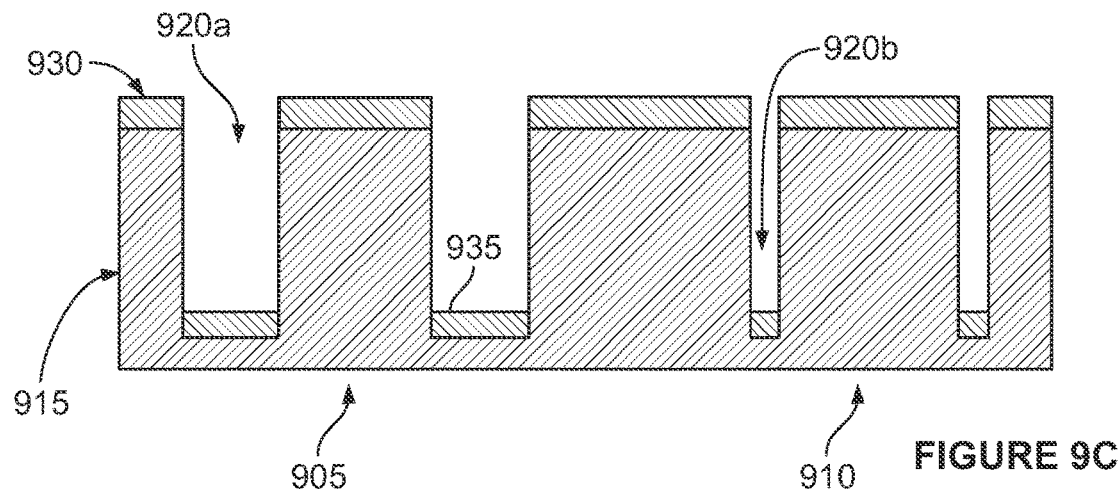
FIG. 9C schematically illustrates a cross-sectional view of the dual or side-by-side surface plasmon resonance-type colorimetric sensor of FIG. 9A with metallic deposits about the tops of the nanoholes at the surface of the base substrate and at the bottom of the nanoholes, in accordance with some embodiments of the invention.

For example, referring to FIGS. 9A through 9C, an exemplary sub-wavelength, nanostructured, plasmon resonance-type colorimetric sensor 900 for detecting the presence of an analyte target molecule(s) is shown. In some variations, the plasmon resonance-type colorimetric sensor 900 may be designed and arrayed to include a plurality of sub-pixels 905, 910. For example, in some implementations, the plasmon resonance-type colorimetric sensor 900 may include a base substrate 915 in which pluralities of metal-insulator-metal (MIM) nanoholes 920a, 920b may be formed. For purposes of illustration and not limitation, the exemplary plasmon resonance-type colorimetric sensor 900 shown in FIGS. 9A through 9C includes a first grouping of MIM nanoholes 920a, e.g., in a first sub-pixel 905, and a second grouping of MIM nanoholes 920b, e.g., in a second sub-pixel 910.

As illustrated, in some embodiments, the nanoholes 920a of the first sub-pixel 905 may be wider (or thicker) and arranged with a greater or longer periodicity than the nanoholes 920b of the second sub-pixel 910. The differing diameters and periodicity between the nanoholes 920a of the first sub-pixel 905 and the nanoholes 920b of the second sub-pixel 910 cause the respective subpixels 905, 910 to reflect or scatter light having a different wavelength and, hence, color.

For purposes of illustration and not limitation, the first sub-pixel 905 includes four nanoholes 920a arrayed in a 2×2 grid and the second sub-pixel 910 also includes four nanoholes 920b arrayed in a 2×2 grid. Either or both the first sub-pixel 905 and the second sub-pixel 910 may include fewer or more nanoholes arranged in smaller or larger grids. In some variations, each nanohole 920a, 920b may be nanometer-sized, i.e., sub-wavelength. Each nanohole 920a, 920b may extend between a metallic surface 930 on a top surface of the substrate 915 and a metallic surface 935 at a bottom of the nanohole 920a, 920b. For ease of illustration, the metallic surfaces 930, 935 are only shown in FIG. 9C, although in practice the metallic surfaces 930, 935 would be present in each of the devices depicted in FIGS. 9A, 9B, and 9C. Each metallic surface 930, 935 may be, for example, platinum, gold, silver, aluminum, copper, tungsten, or combinations thereof. These metallic surfaces 930, 935, separated by the nanoholes 920a, 920b, provide and/or define vertical limits for collecting and focusing incident light. Advantageously, the plasmonic sub-pixels 905, 910 may be configured to produce, in the presence of an analyte target molecule and when struck by incident light of a particular wavelength, an observable color change to provide evidence of the presence of the target analyte.

As before, the base substrate 915 may be manufactured from an organic, inorganic, or hybrid MIP material, from a dielectric or insulative material (e.g., silica, titanium dioxide, silicon nitride, and the like) in which the plurality of surfaces defining the nanoholes are coated with a MIP or aptamer material or other binding material such as coordination complex, or from a metallic material (e.g., gold, silver, aluminum, and the like) in which the plurality of surfaces defining the nanoholes are coated with a MIP or aptamer material or other binding material such as coordination complex. Moreover, the surficial walls defining each of the nanoholes in the base substrate 915 may be coated with a hydrophobic material. In such a fashion, if a fluid does not contain an analyte of interest, the MIP cavities do not absorb any analytes of interest, the fluid is repelled by the hydrophobic material, and the fluid is prevented from infiltrating into any of the nanoholes, which therefore remain in an unfilled state. On the other hand, if a fluid does contain the analytes of interest, the MIP cavities absorb the analytes of interest, and the solid-air surface tension, solid-liquid surface tension, and liquid-air surface tension values change (i.e., the wettability of the surficial walls defining the nanoholes changes) to the extent needed to enable infiltration of the fluid into the nanoholes.

In operation and by design, each sub-pixel 905, 910 may be structured and arranged to emit, under a first set of operating conditions (e.g., in the presence of a fluid having no target analyte of interest present therein), scattered light of a certain color that, in combination, produces light of a desired color. For example, under the first set of operating conditions, sub-pixel 905 may emit magenta-colored light and sub-pixel 910 may emit yellow-colored light, which, when mixed together, produces red-colored light. Under a second set of conditions (e.g., in the presence of a fluid having target analytes of interest present therein), however, each sub-pixel 905, 910 may be structured and arranged to emit scattered light of a certain color that, in combination, provides a desired color change (e.g., from red to blue) in the plasmonic-resonance-based colorimetric sensor 900.

In yet another embodiment, and with reference now to FIGS. 13A-13D, a colorimetric nanosensor device 1300 may include an array of single plasmonic color pixels 1301. Each single plasmonic color pixel 1301 may include a metal, rectangular-shaped nanoblock 1303 positioned on top of a dielectric nanopillar 1302. Each nanopillar 1302 may be positioned in an opening of a perforated metal back reflector 1305. As a non-limiting example, the sensor 1300 can be made by depositing metal on top of an array of dielectric nanopillars 1302. A gap between adjacent nanopillars 1302 can be tuned from one (1) nm to one (1) mm and these narrow gaps can form deep interconnected nanofluidic grooves 1310 as sensing channels, Each plasmonic color pixel 1301 may include a hydrophobic coating as well as a MP or aptamer coating or a coating of other binding materials such as coordination complex. FIGS. 14A and 14B demonstrate how the sensor 1300 operates to detect a fluid containing an analyte of interest. With reference to FIG. 14A, because the sensor surface is hydrophobic, a fluid 1401 that does not include the analyte of interest is not able to penetrate through the grooves 1310 (i.e., a Cassie-Baxter wetting mode may be observed). In contrast, with reference to FIG. 14B, a fluid 1401W that contains the analyte of interest causes a wettability of the sensor surface to change due to the binding of analytes to the sensor surface. As such, a, full fluid penetration or partial penetration into the grooves 1310 is triggered (i.e., a Wenzel wetting mode may be observed). As a result, a color change and/or spectra change (reflection spectra, scattering spectra, or transmission spectra) may be observed.

Additional Testing

In the case of the plasmonic-resonance-based colorimetric sensors, further verification of the presence of the analyte target molecule of interest is possible by subjecting the sensors to additional testing that does not lend itself to use in the field. More particularly, surface-enhanced Raman scattering (SERS) is a spectroscopic method used in chemical and/or biological sensing for the purpose of detecting individual molecules, e.g., analyte target molecules. Raman scattering, using a spectrometer capable of detecting a molecular vibrational spectrum, is predicated on the notion that any molecule of each analyte target will have a unique Raman scattering spectrum, displaying, upon illumination, e.g., by a laser light-emitting device, discrete, specific (Raman) peaks that can be collected and used to identify or confirm the presence of the analyte target molecule with a high degree of accuracy. Generally, a Raman signal is extremely weak and it is very difficult to detect. However, the Raman signal may be greatly enhanced due to the strong local electromagnetic field generated from plasmonic arrays. Therefore, a sensitive detection at a low concentration of analyte becomes possible.

Sensors for Combined Dielectric Structural Color and Plasmonic Resonance Use

The colorimetric sensors described above have been described for either dielectric structural color or metallic plasmon resonance applications. Those of ordinary skill in the art, however, can appreciate that the two sensor types also may be combined on a single substrate, such that a single base substrate includes one portion that provides a colorimetric response associated with dielectric structural color and another portion that provides a colorimetric response associated with surface plasmonic resonance resulting from metallic nanostructures.

In addition, in various embodiments, the MIPs described herein can define multiple cavities for multiple, different analytes, such that a single one of the sensors described herein can detect the presence of multiple, different analytes. Alternatively, in certain embodiments, a sensor described herein may be configured to detect the presence of only a single analyte, but multiple ones of such sensors may be used in tandem such that, together, the sensors can detect the presence of multiple, different analytes.

Methods of Manufacturing the Plasmonic-Resonance-Based Colorimetric Sensors

Figure 10:
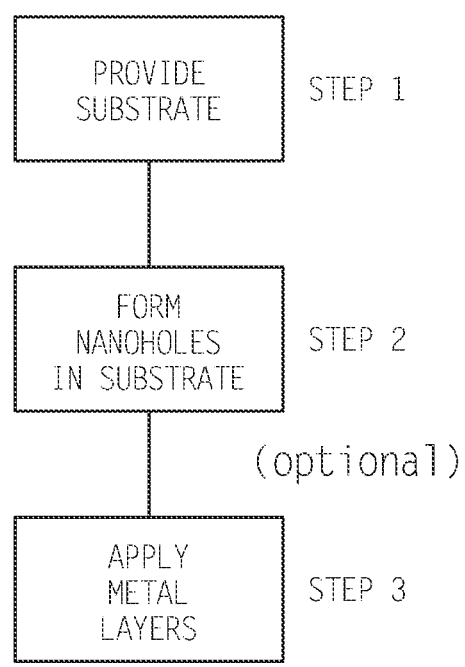
FIG. 10 shows an exemplary flow chart for manufacturing structural color-type colorimetric sensors or surface plasmon resonance-type colorimetric sensors, in accordance with some embodiments of the invention.

Referring again to FIGS. 8A and 8B and the flow chart depicted in FIG. 10, one exemplary method of producing a surface plasmon resonance-type colorimetric sensor is shown. In STEP 1, the base substrate 810, of desired dimensions and volume, is provided. Then, in STEP 2, a plurality of nanoholes 805 are formed in the base substrate 810. Design parameters may include, but are not limited to: the size (e.g., diameter) and depth of the nanoholes 805, the periodicity between the nanoholes 805, and so forth.

In some applications, the nanoholes may be formed in the base substrate in a top down fashion by etching or otherwise removing material from the base substrate. Exemplary methods of etching include, for the purpose of illustration and not limitation, electrochemical etching, wet etching, dry etching, and laser-induced etching.

For example, reactive ion etching, which can involve a wet or a dry etching process, may be employed to form the nanoholes in the base substrate. In accordance with one method, a pattern mask may be applied to a surface(s) of the base substrate. The mask may be positive or negative. A positive mask typically protects those portions of the substrate that will remain after the etching process, while a negative mask is employed to remove those portions of the substrate that have been masked. Once the mask is applied to the base substrate, the masked surface(s) of the base substrate may be exposed, e.g., in a vacuum chamber, to a bombardment of reactive ions. The ion bombardment removes material from the base substrate to form the nanoholes.

As another non-limiting example, a high energy laser may be employed in a laser-induced etching process to form precise nanoholes in the base substrate by etching away the material in the base substrate.

With reference again to FIG. 10, STEP 2 also involves applying a hydrophobic coating to the surficial walls defining each of the nanoholes and (if the base substrate is not itself a MIP) applying a MIP layer as a coating to the surficial walls defining all or a select number of the nanoholes. Both the hydrophobic coating and the MIP coating may be applied to the applicable surfaces as explained above in the section describing the methods of manufacturing the structural-color-based colorimetric sensors. As also explained above, in certain embodiments, the MIP coating can be replaced by a coating of aptamers or other binding materials such as coordination complex that specifically bind to analyte molecules.

Next, in STEP 3 of FIG. 10, a thin layer (e.g., of about 0.1 nm to several hundred nanometers) of metal (e.g., platinum, gold, silver, aluminium, copper, tungsten, combinations thereof, and the like) may be applied (e.g., by metal deposition, chemical vapor deposition (CVD), sputtering, three-dimensional nanoprinting, plasma-enhanced chemical vapor deposition (PECVD), physical vapor deposition (PVD), electroless plating, and so forth) on the top surface of the base substrate, as well as on the bottom surface of each nanohole. Deposition on the top surface of the base substrate may form a continuous metal film atop the substrate and about the array of nanoholes. In the alternative, an annular metal nanodisk concentric with or substantially concentric with the opening of each nanohole may be formed on the top surface of the substrate about each nanohole opening. Extra MIP or aptamer materials or other binding materials such as coordination complex may be applied as a coating to the metal surfaces.

Figure 11A:
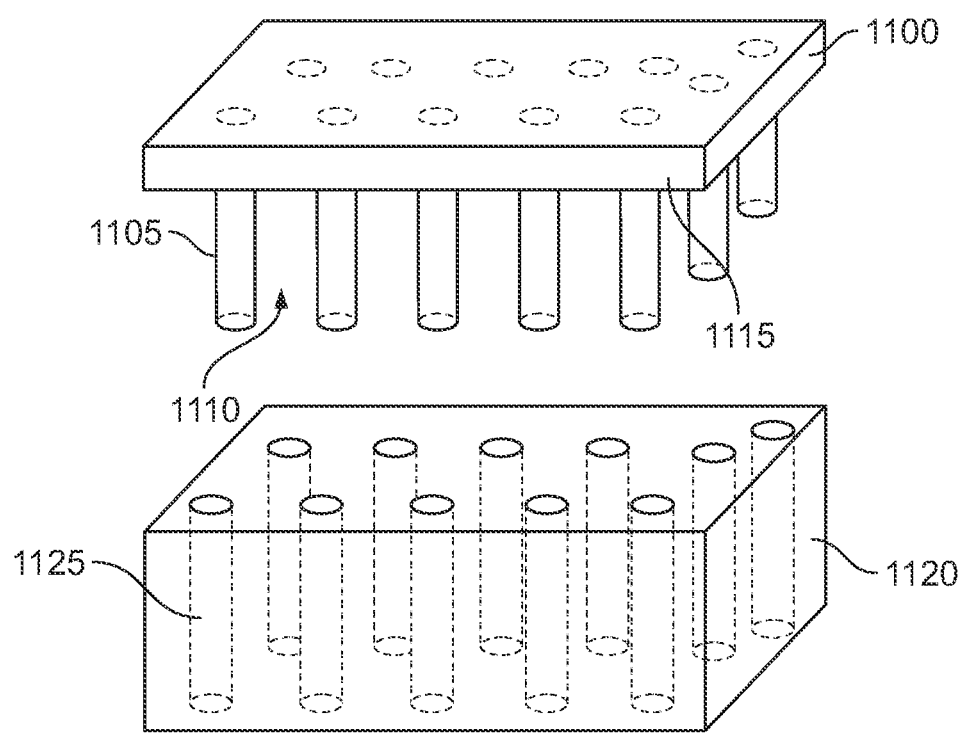
FIG. 11A schematically illustrates a step in a method of manufacturing a plasmonic colorimetric sensor, in accordance with some embodiments of the invention.

Referring now to FIG. 11A, as an alternative to the etching process, in another exemplary method of manufacture, a surface plasmon resonance-type colorimetric sensor may be manufactured using a mold 1100. The mold 1100 may be made of, for example, silicone or some other suitable mold material such as silicon (Si), polyethylene terephthalate (PET), a UV-curable resin, and the like. In some implementations, the mold 1100 is structured and arranged to include, on a bottom portion 1115 thereof, solid portions 1105 with openings 1110 therebetween. The solid portions 1105 are structured and arranged to provide a negative or mirrored image of a desired array of nanoholes 1125 in a base substrate 1120. As will be appreciated by those of ordinary skill in the art, although FIG. 11A shows a method in which the solid portions 1105 are formed on the bottom portion 1115 of the mold 1100 and the bottom portion is pressed into a top surface of the base substrate 1120, the solid portions 1105 may, instead, be formed on a top portion of the mold 1100 and the top portion pressed into the base substrate 1120.

The solid portions 1105 may be configured to provide, in the base substrate 1120, a resulting array of nanoholes 1125 that each has a desired size, shape, depth, periodicity, and so forth. Although the shape and size of each solid portion 1105 may be the same or substantially the same as one another, those of ordinary skill in the art will appreciate and understand that the solid portions 1105 may instead be sized and shaped differently from one another so as to provide nanoholes of differing sizes, shapes, and depths, and of differing periodicity. For example, with reference to the colorimetric sensors depicted in FIGS. 9A through 9C, the solid portions 1105 may have non-uniform dimensions and differing periodicities, so as to produce a first sub-pixel 905 with wider (i.e., thicker), less densely-spaced nanoholes 920a and a second sub-pixel 910 with thinner, more closely-spaced nanoholes 920b.

Figure 11B:
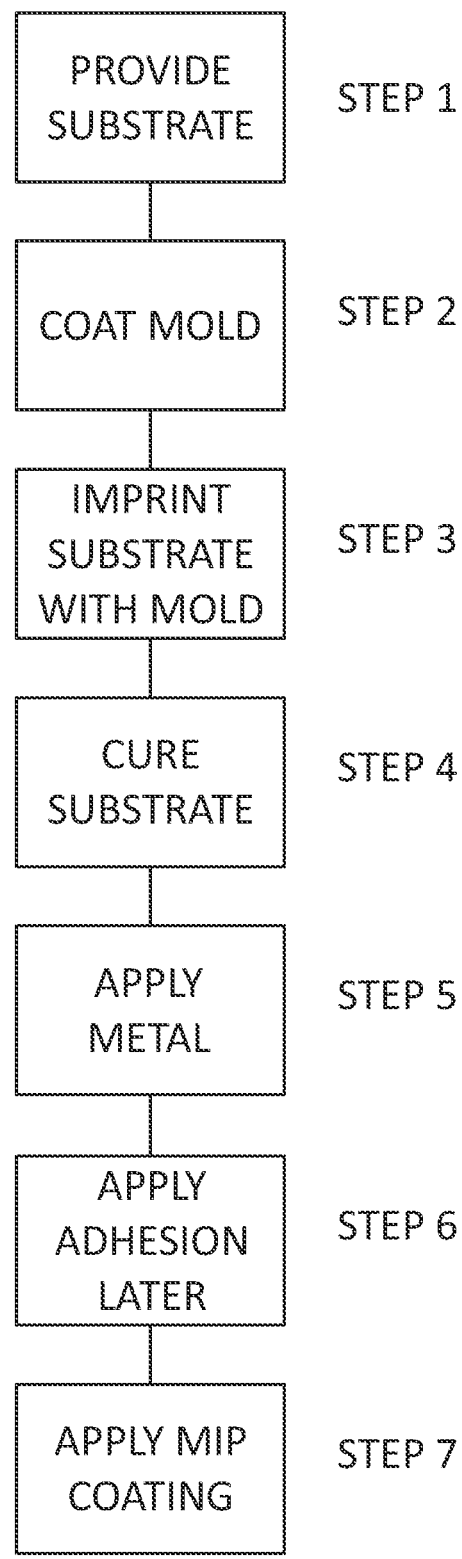
FIG. 11B shows an exemplary flow chart for manufacturing the colorimetric sensor shown in FIG. 11A.

In accordance with an exemplary method, and with reference now also to FIG. 11B, after providing the base substrate 1120 and mold 1100 (STEP 1), the surfaces of the solid portions 1105 of the mold the mold 1100 may be coated (STEP 2) with a very thin layer of a releasing agent, e.g., fluorocarbon, fluorosilane, polybenzoxazine, combinations thereof, and the like to facilitate removal of the mold 1100 from the resulting array of nanoholes 1125. The very thin layer or coating of the releasing agent can be a self-assembled monolayer (SAM) or multiple layers with a thickness from less than about one (1) Angstrom to about 10 nm. The base substrate 1120 is then imprinted with the mold 1100 (STEP 3).

Following the imprinting of the nanoholes 1125 in the base substrate 1120 and depending on the material used to manufacture the base substrate 1120, the imprinted substrate 1120 may be cured (STEP 4) via photo- (e.g., using ultraviolet (UV) light) or thermal-initiated polymerization.

In a next step, a thin layer (e.g., of about 0.1 nm to several hundred nanometers) of metal (e.g., platinum, gold, silver, aluminium, copper, tungsten, combinations thereof, and the like) may be applied (STEP 5) (e.g., by metal deposition, chemical vapor deposition (CVD), sputtering, three-dimensional nanoprinting, plasma-enhanced chemical vapor deposition (PECVD), physical vapor deposition (PVD), electroless plating, and so forth) on the top surface of the base substrate 1120, as well as on the bottom surface of each nanohole 1125. Deposition on the top surface of the base substrate 1120 may form a continuous metal film atop the substrate 1120 and about the array of nanoholes 1125. In the alternative, an annular metal nanodisk concentric with or substantially concentric with the opening of each nanohole 1125 may be formed on the top surface of the substrate 1120 about each nanohole 1125 opening.

As before, a hydrophobic coating may then be applied to the surficial walls defining each of the nanoholes 1125 and (if the base substrate 1120 is not itself a MIP) a MIP layer may be applied as a coating to the surficial walls defining all or a select number of the nanoholes 1125. Both the hydrophobic coating and the MIP coating may be applied to the applicable surfaces as explained above in the section describing the methods of manufacturing the structural-color-based colorimetric sensors. As another example, in the case where the nanoholes 1125 are formed in a dielectric material to be coated with a MIP material (i.e., where the base substrate 1120 is not itself a MIP), a thin (e.g., 0.1 nm to 100 nm thick) adhesion layer of silica may be applied (e.g., via atomic layer deposition (ALD), chemical vapor deposition (CVD), physical vapor deposition (PVD), electron beam evaporation, or sputtering) to the surficial walls of the nanoholes 1125 (STEP 6). Subsequently, a soluble and processable MIP may be applied (e.g., via spin-coating or dip-coating) to the silica surface as a thin (e.g., 0.1 nm to 100 nm thick) coating (STEP 7). In certain embodiments, the MIP coating can be replaced by a coating of aptamers or other binding materials such as coordination complex that specifically bind to analyte molecules.

Figure 13C:
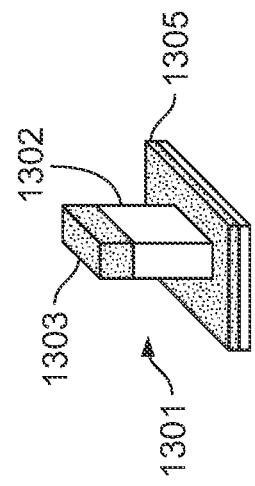
FIG. 13C schematically illustrates a single plasmonic pixel, in accordance with some embodiments of the invention.
Figure 13D:
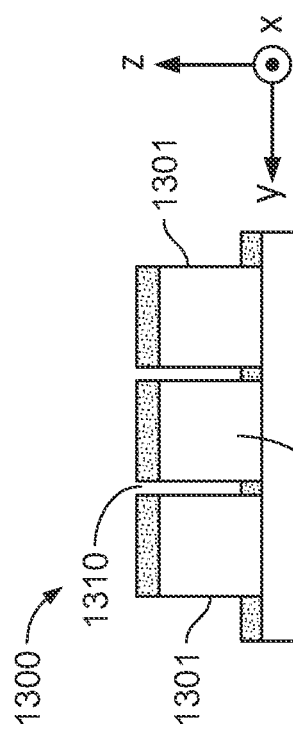
FIG. 13D schematically illustrates a side view of the array of nanopillars shown in FIGS. 13A and 13B, but with metal present, in accordance with some embodiments of the invention.
Figure 13A:
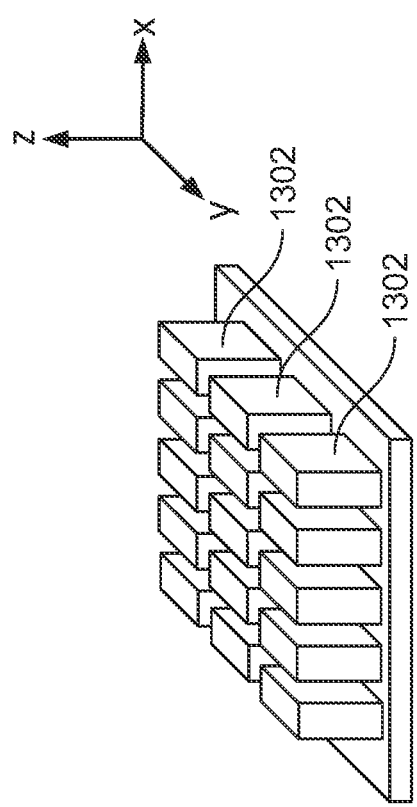
FIG. 13A schematically illustrates a top perspective view of an array of nanopillars without metal present, in accordance with some embodiments of the invention.
Figure 13B:
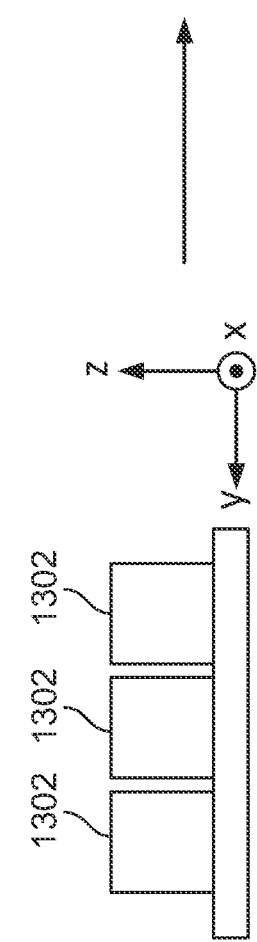
FIG. 13B schematically illustrates a side view of the array of nanopillars without metal present shown in FIG. 13A.
Figure 15:
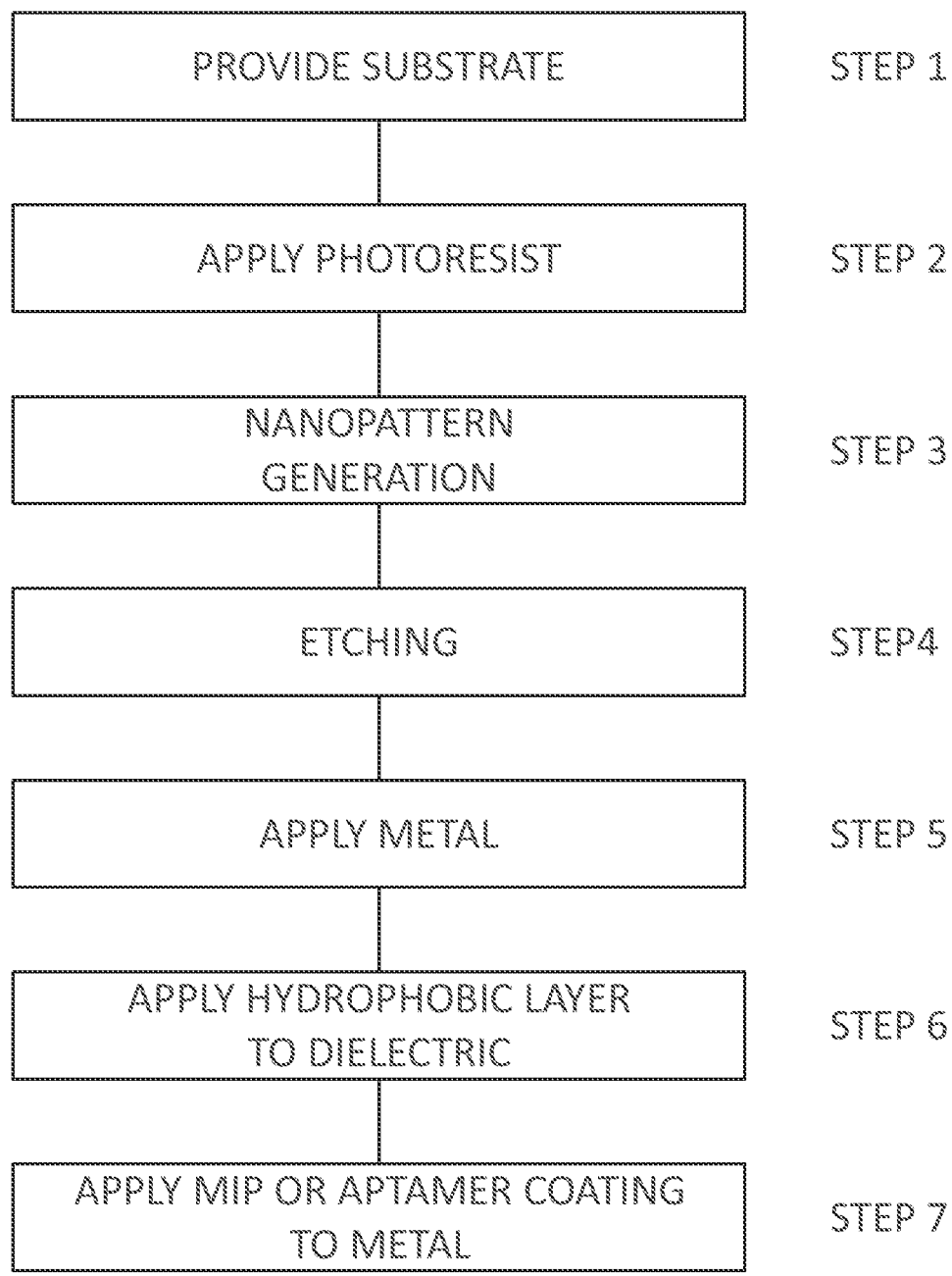
FIG. 15 shows an exemplary flow chart for manufacturing the colorimetric sensor shown in FIG. 13D.

Referring now to the flow chart depicted in FIG. 15, one exemplary method of producing the surface plasmon resonance-type colorimetric sensor depicted in FIGS. 13D, 14A, and 14B is shown. After providing a base substrate (STEP 1) and applying a photoresist layer (STEP 2), a nanopattern with predetermined geometry can be generated and transferred to the photoresist layer via electron-beam lithography (EBL) and an etching process (STEPS 3 and 4). Nanopillars 1302 may be formed after etching part of the photoresist layer or etching into the base substrate. In a next step, a thin layer (e.g., of about 0.1 nm to several hundred nanometers) of metal (e.g., platinum, gold, silver, aluminium, copper, tungsten, combinations thereof, and the like) may be applied (STEP 5) (e.g., by metal deposition, chemical vapor deposition (CVD), sputtering, three-dimensional nanoprinting, plasma-enhanced chemical vapor deposition (PECVD), physical vapor deposition (PVD), electroless plating, and so forth) on the top surfaces of the nanopillars 1302, as well as on the bottom surface of each nanofluidic groove 1310. A hydrophobic coating may then be applied to the walls of the nanopillars 1302 (STEP 6). A MIP layer can be either grafted from the metal surface 1303 or grafted to the metal surface 1303 (STEP 7). Alternatively, an aptamer layer or layer of other binding material such as coordination complex can be attached to the metal surface 1303 (STEP 7).

Practice of the invention will be more fully understood from the following example, which is presented herein for illustrative purposes only, and should not be construed as limiting the invention in any way.

Example

Figure 12:
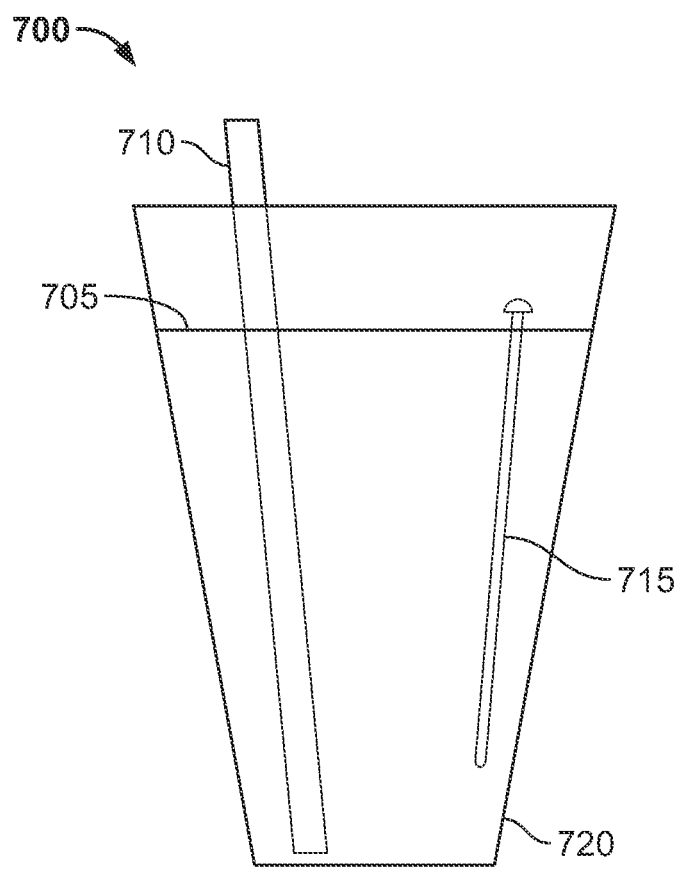
FIG. 12 schematically illustrates exemplary structures for use in combination with colorimetric sensors for detecting an analyte target molecule of interest in a fluid sample, in accordance with some embodiments of the invention.

In various embodiments, for example referring to FIG. 12, any of the sensors or sensor arrays described herein may be operatively disposed upon or integrated within a surface of a substrate 700. In its normal or customary use, the substrate 700, the surface thereof, and the sensor or sensor array disposed upon or integrated within that surface are exposed to a liquid 705 in which an analyte target molecule of interest may or may not be present. For the purpose of illustration and not limitation, exemplary substrates 700 include a straw 710, a swizzle stick or stirrer 715, a fluid receptacle 720 (e.g., a cup, a glass, and the like), and so forth.

In a first step, a fluid sample to be interrogated, e.g., a beverage, is brought into contact with the sensor or sensor array. This may occur, for example, by pouring the beverage into a fluid receptacle into which the sensor or sensor array has been integrated; by inserting a straw, stirrer, or swizzle stick into which the sensor or sensor array has been integrated into the beverage; and so forth. In some applications, visual indicia of the sensor or sensor array after initial contact with the beverage may provide a neutral or "safe" reading, e.g., the sensor or sensor array may emit blue light. If an analyte of interest is introduced into the beverage, a color change in the sensor or sensor array, e.g., from blue to red, indicates that analyte is present in the fluid sample. Thus, in a second step, the sensor or sensor array produces a color change when it comes into contact with the beverage. Advantageously, the sensor or sensor array may be able to detect the presence of an analyte of interest for an extended period of time, such that a single sensor or sensor array may be used to continue to detect for hours whether or not an analyte of interest is present in the beverage.

INCORPORATION BY REFERENCE

The entire disclosures of each of the patent documents and scientific articles cited herein are incorporated by reference herein in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of manufacturing a sensor capable of detecting an analyte of interest in a fluid sample, the method comprising:
    mixing a liquid precursor of a polymer material with a plurality of analytes of interest to create a mixed liquid precursor of the polymer material;
    co-assembling the mixed liquid precursor of the polymer material with a plurality of templates to create a co-assembly;
    solidifying the co-assembly to create a solidified co-assembly;
    removing the plurality of templates from the solidified co-assembly to create a plurality of surfaces for the solidified co-assembly, each surface defining respective voids in the solidified co-assembly;
    removing the plurality of analytes from the solidified co-assembly to create a binding material to receive the plurality of analytes of interest; and
    coating the plurality of surfaces with a hydrophobic material, such that each surface of the plurality of surfaces has an initial hydrophobicity so as to repel a first fluid sample that does not contain the plurality of analytes of interest, which prevents the first fluid sample from infiltrating the respective voids defined by the each surface of the plurality of surfaces,
    wherein the sensor is configured such that, when the plurality of analytes of interest in a second fluid sample contacts the binding material, a wettability of at least one surface of the plurality of surfaces changes to a degree great enough to overcome the initial hydrophobicity and allows infiltration of the second fluid sample containing the plurality of analytes of interest into the respective voids defined by the each surface of the plurality of surfaces.

2. The method of claim 1, wherein each template of the plurality of templates is substantially spherically shaped.

3. The method of claim 1, wherein the respective voids are spherically shaped.

4. The method of claim 1, wherein each template of the plurality of templates is cylindrically shaped.

5. The method of claim 1, wherein the respective voids are cylindrically shaped.

6. The method of claim 5 further comprising positioning metal at a bottom of the respective voids and outside a top of the respective voids.

7. The method of claim 1, wherein at least two voids of the respective voids are interconnected.

8. The method of claim 1, wherein the respective voids are isolated from one another.

9. The method of claim 1, wherein solidifying the co-assembly comprises positioning the plurality of templates to have a periodic distribution.

10. The method of claim 9, wherein neighboring templates of the plurality of templates are spaced apart by a distance between 1 nanometer and 5000 nanometers.

11. The method of claim 9, wherein neighboring templates of the plurality of templates are spaced apart by a distance corresponding to a wavelength range of visible light.

12. The method of claim 1, wherein the co-assembly is solidified via at least one of a thermal treatment, a photo-induced solidification, a radiation-induced solidification, or a chemical-reaction-induced solidification.

13. The method of claim 1, wherein the liquid precursor of the polymer material is an organic polymer.

14. The method of claim 1, wherein the liquid precursor of the polymer material is an inorganic polymer.

15. The method of claim 1, further comprising disposing the sensor upon or integrating the sensor within a surface of one of a straw or a stirrer.

16. The method of claim 1, further comprising disposing the sensor upon or integrating the sensor within a surface of a fluid receptacle.

17. The method of claim 16, wherein the fluid receptacle is one of a cup or a glass.

18. A method of manufacturing a sensor capable of detecting an analyte of interest, the method comprising:
    creating a plurality of surfaces of the sensor, each surface of the plurality of surfaces defininig a respective void and having a binding material that binds the analyte of interest;
    coating the plurality of surfaces with a hydrophobic material, such that the each surface of the plurality of surfaces has an initial hydrophobicity so as to repel a first fluid sample that does not contain the analyte of interest, which prevents the first fluid sample from infiltrating the respective voids defined by the each surface of the plurality of surfaces,
    wherein the sensor is configured such that: when the analyte of interest in a second fluid sample contacts the binding material, a wettability of at least one surface of the plurality of surfaces changes to a degree great enough to overcome the initial hydrophobicity and allows infiltration of the second fluid sample containing the analyte of interest into the respective voids defined by the each surface of the plurality of surfaces.

19. The method of claim 18, wherein the binding material is a coordination complex.

20. The method of claim 18, wherein the binding material is an aptamer.

* * * * *